(12) United States Patent
Fontaine et al.

(10) Patent No.: US 11,442,008 B2
(45) Date of Patent: Sep. 13, 2022

(54) SYSTEMS AND METHODS FOR MEASURING STRESS-BASED CHARACTERISTICS OF A GLASS-BASED SAMPLE

(71) Applicant: CORNING INCORPORATED, Corning, NY (US)

(72) Inventors: Norman Henry Fontaine, Painted Post, NY (US); Vitor Marino Schneider, Painted Post, NY (US); Jayantha Senawiratne, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 229 days.

(21) Appl. No.: 16/944,748

(22) Filed: Jul. 31, 2020

(65) Prior Publication Data

US 2021/0033530 A1    Feb. 4, 2021

Related U.S. Application Data

(60) Provisional application No. 62/881,001, filed on Jul. 31, 2019.

(51) Int. Cl.
*G01N 21/41* (2006.01)
*G01N 21/01* (2006.01)

(52) U.S. Cl.
CPC ............. *G01N 21/41* (2013.01); *G01N 21/01* (2013.01); *G01N 2021/0162* (2013.01); *G01N 2201/025* (2013.01); *G01N 2201/06113* (2013.01)

(58) Field of Classification Search
CPC .... G01N 21/958; G01N 21/01; G01N 21/896; G01N 21/23; G01N 21/41;
(Continued)

(56) References Cited

U.S. PATENT DOCUMENTS

2005/0023434 A1*  2/2005  Yacoubian ......... G01N 29/2418
                                                        250/200
2005/0024627 A1*  2/2005  Junnarkar ............. G01M 11/35
                                                        356/73.1
(Continued)

OTHER PUBLICATIONS

International Search Report and Written Opinion of the International Searching Authority; PCT/US2020/043831; dated Oct. 8, 2020; 13 Pages; European Patent Office.

*Primary Examiner* — Sang H Nguyen

(57) ABSTRACT

The systems and methods include generating polarization-switched (PS) detector and reference signals using a polarization switch controlled by a digital control signal generated by digital input/output card. A gain adjustment is performed on the PS detector and reference signals to define gain-adjusted detector and reference signals. The digital control signal is used to synchronize the gain-adjusted PS detector and reference signals to define gain-adjusted synchronized PS detector and reference signals each having respective steady-state portions. The steady state portions are used to define a measurement signal. The measurement signal is then used to calculate a stress-based characteristic of the sample being measured. The sample can be moved continuously or discretely through different measurement positions, which are synchronized with the operation of the polarization switch using the digital control signal.

29 Claims, 19 Drawing Sheets

(58) Field of Classification Search
CPC ... G01N 2021/8848; G01N 2021/0162; G01N 2201/025; G01N 2201/06113; G01N 33/386; G01L 1/24
See application file for complete search history.

(56) References Cited

U.S. PATENT DOCUMENTS

| | | |
|---|---|---|
| 2005/0128469 A1 | 6/2005 | Hall et al. |
| 2005/0154300 A1* | 7/2005 | Wodnicki ............... B06B 1/0215 600/459 |
| 2011/0201936 A1* | 8/2011 | Miyajima ........... G01S 7/52023 600/459 |
| 2013/0321818 A1* | 12/2013 | Yao ........................ G01N 21/23 356/477 |
| 2014/0118740 A1 | 5/2014 | Fontaine et al. |
| 2015/0116713 A1 | 4/2015 | Roussev et al. |
| 2017/0291849 A1 | 10/2017 | Dejneka et al. |
| 2019/0025141 A1* | 1/2019 | Liu ........................ G01L 1/241 |

\* cited by examiner

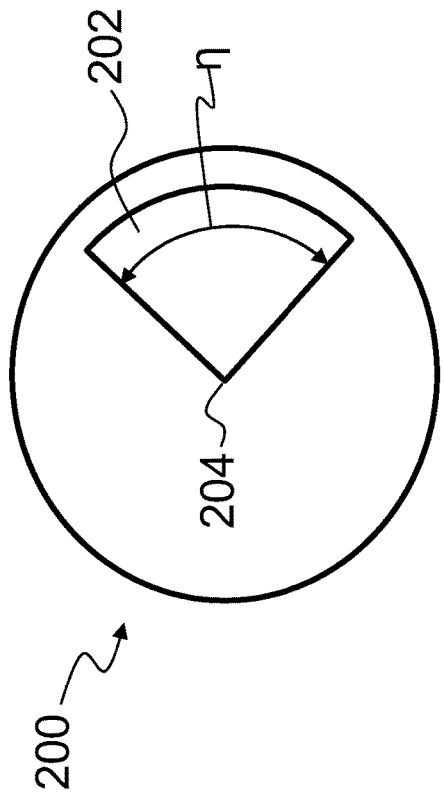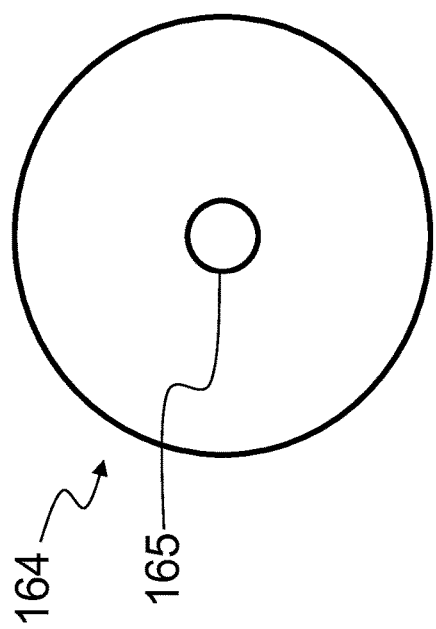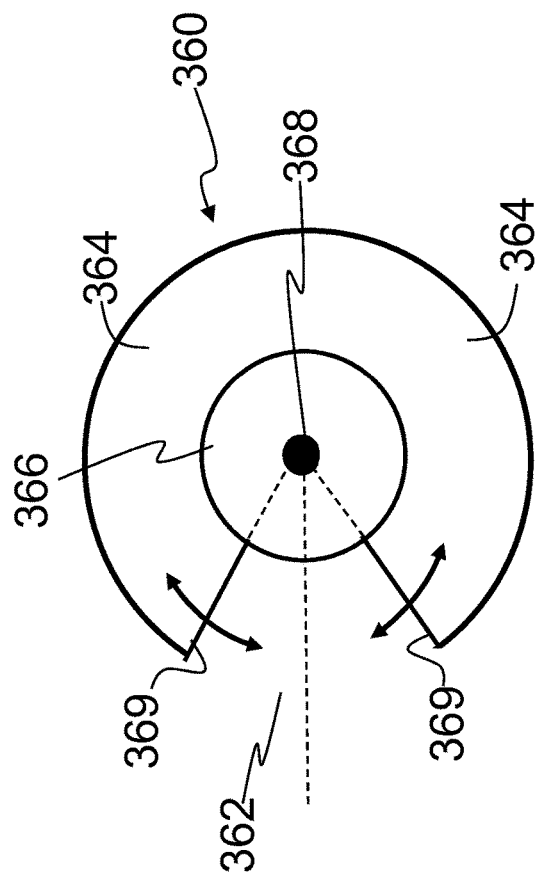

SYSTEMS AND METHODS FOR MEASURING STRESS-BASED CHARACTERISTICS OF A GLASS-BASED SAMPLE

This application claims the benefit of priority of U.S. Provisional Application Ser. No. 62/881,001 filed on Jul. 31, 2019 the content of which is relied upon and incorporated herein by reference in its entirety.

FIELD

The present disclosure relates to systems and methods for optically characterizing glass, and in particular relates to systems and methods for measuring stress-based characteristics of a glass-based sample.

BACKGROUND

Ion-exchange and other strengthening processes can create stresses in a glass-based sample and give rise to optical birefringence. Compressive and tensile stress regions formed in the material that makes up the glass-based sample can have relatively small depths (e.g., 10 micrometers) or relatively large depths (e.g., a few or many millimeters). The stress profile of a glass-based sample can be deduced from the measurement of the refractive index profiles for orthogonal polarizations of measurement light, with the difference in the index profiles for both polarization states representing the birefringence. The stress is related to the birefringence through the stress-optic coefficient. The character (profile) of the stress can be quite complex and depends on a number of factors, including the nature of the glass-based material, the production processes used to make the glass-based sample and the down-stream manufacturing process.

The stresses in a glass-based sample can be altered by various external forces, including how the glass-based sample is mounted into a device and how the glass-based sample is used. During reliability and failure-mode studies, various quality-control procedures are used to test and measure the change in stress across the edges and throughout the volume of the glass-based sample.

One technique that has been used to measure refractive index and birefringence profiles (and thus stress) in ion-exchanged, planar optical waveguides is the refracted near-field (RNF) method. The RNF method utilizes a system wherein a reference block is in contact with the glass-based sample being measured. Measurement light passes through the glass-based sample and the reference block and is detected by a photodetector arranged very close to the top of the reference block. An example RNF system is disclosed in U.S. Pat. No. 5,280,334, which is incorporated by reference herein.

A problem with prior-art RNF systems is that the photodetector, besides detecting the measurement light, also detects scattered and multiply reflected light from many angles and locations. The scattered light may arise from imperfections in an index fluid (e.g., contaminants), on the surfaces of the reference block (e.g., dust leftover after sub-optimal cleaning), in the optics of the RNF system or even within the sample itself (e.g., bubbles and other "seeds"). Such scattered light may lead to erroneous measurements of the refracted power of the glass part. Other problems with prior-art RNF systems include the inability to make a large number of measurements of a glass-based sample and then process all of the measurement data in a timely and efficient manner. This shortcoming adversely impacts manufacturing since the stress measurements are used for process and quality control.

SUMMARY

The disclosure is directed to improved RNF systems and methods for measuring a stress-based characteristic of a glass-based sample (referred to hereinafter as a "sample.") Example stress-based characteristics include refractive index profiles for orthogonal polarizations of light (i.e., transverse electric (TE) refractive index $n_{TE}(x)$ and the transverse magnetic (TM)) refractive index $n_{TM}(x)$), birefringence profile $B(x)$, and the stress profile $S(x)$, where the x-coordinate is the depth into the sample. The stress characteristic can include the surface (compressive) stress $S(0)$, the knee stress $S_k(x_k)$, birefringence B, and the center tension CT. The systems and methods can characterize stress to within 1 megapascal (MPa).

The improved systems and methods current invention can be used to measure stress-based characteristics of any materials for which the light can propagate with low to moderate attenuation and where a measurement signal can be effectively detected. The systems and methods disclosed herein allow for rapid evaluation of the stress and the index profiles of glass, glass-ceramics, crystals, and other transparent materials, collectively referred to herein as "glass-based material" or "glass-based samples." Rapid measurements are useful because they can provide much needed feedback for process quality control and process feedback used to form the samples, and for new material development. The systems and methods disclosed herein enable characterization of one or more stress-based characteristics with high precision and accuracy and at much faster speeds than prior art systems and methods.

One type of sample strengthening technique is ion exchange (IOX) wherein external ions are used to replace native ions in the sample material, wherein the ions typically have a substantially different size (e.g., larger external $K^+$ replacing smaller native $Na^+$ ions). An IOX process carried out on a sample causes a localized change of the composition inside the sample material. The change in composition can generate localized stresses in the regions where the ions are replaced. The appearance of such localized stresses leads to localized birefringence, which is directly related to the imparted stress via the stress-optic coefficient (SOC) of the material. The stress regions depend on the ion exchange conditions and the material properties of the sample, e.g., the nature of the glass matrix for a glass sample. In this case, both compressive and tensile regions can be created near the sample surface through which the IOX process takes place. Some of the regions of compression or tension can be relatively narrow, depending on the IOX process used, and in examples can range from a few microns to hundreds of microns. Consequently, high spatial resolution is needed to accurately measure narrow regions of stress and birefringence and related stress-based characteristic in a transparent material across its thickness (i.e., into the depth of the sample).

There are other processes beyond an IOX process that can lead to the formation of stress in materials that require characterization. These can include ion implantation, thermal annealing, and lamination among others.

The example systems and method disclosed herein have one or more of the following advantageous features and capabilities:

1) A high speed achromatic ferroelectric liquid crystal (FLC) polarization rotator used as a high-speed polarization switch, with its operation synchronized with the measurement and reference signal detection process using an external TTL (Transistor-Transistor Logic) signal. This feature enables switching of the polarization state of the laser light at frequencies as high as 5000 Hz. Therefore, the measurement time for a single point on the sample can be reduced to below 1 millisecond (ms). For example, at a FLC-based switching frequency of 5 KHz, the measurement time is only 0.2 ms (i.e., 1/5000 Hz=0.2 ms).

2) An input/output (I/O) controller configured for high speed data acquisition. An example I/O controller includes an analog input card (e.g. NI-9222 or NI-9223), which can acquire data at a speed of 0.5 and 1 Msample/second/channel, respectively. The example I/O controller also includes a digital output card (e.g. NI 9401 with 8 DIO, 5 V/TTL, Bidirectional, 100 ns) for providing a modulation signal to the FLC polarization switch to provide the aforementioned fast switching of the polarization state of the input polarized light beam. Both the analog and digital I/O cards can be inserted into to NI cDAQ (cDAQ-9178) or NI-cRIO (NI-cDAQ-9045) chassis and be controlled remotely through software, such as LabVIEW® software or other software platforms, such as C-sharp.

3) One or more piezoelectric based friction-driven motion stages to provide precise, steady and uniform motion, thereby enabling substantially vibration-free and accurate position measurements for both 1-D and 2-D imaging.

4) a blue laser source, which provides a blue laser of wavelength 405 nm. This allows for improved spatial resolution as compared to the use of red wavelengths (e.g., 632 nm). The blue measurement wavelength allows for characterizing stress-based characteristics much closer to the surface of the sample than for longer wavelengths, such as red wavelengths. In an example, the laser source is configured to emit both blue and red wavelengths to obtain measurements at these two different wavelengths.

5) Operation of the system in a step mode or in continuous mode.

6) Operation of the system to measure either a one-dimensional (1D) profile or a two-dimensional (2D) profile of a given stress-based characteristic.

The systems and methods can have some or all of the following features and advantages:

Operation of the system in the continuous mode leads to a significant improvement in the measurement speed. By way of example: measurement of a 1 mm thick sample at a sample speed of 0.1 mm/s can be completed in 10 s with a sampling interval of one data point per micron; measurement of a 1 mm thick sample with a 0.5 mm/s sample speed can be completed in 20 s with a sampling interval of one data point per 500 nm. Measurement of a 1 mm thick sample with a 0.02 mm/s sample speed can be completed in 50 s with a sampling interval of one data point per 200 nm.

Operation of the system in the step mode allows for fast and precise measurements. In an example, a polarization switching speed of 1000 Hz reduces the measurement time per single point 1 millisecond (ms), i.e., it takes 1 ms to measure the TE and TM measurement light from a single point on the sample. The total measurement time is dictated by the stepping time and the number of steps used in the measurement. For example, the stepping time can be in the range of 50 ms or higher per step. A measurement using 1000 steps has a total measurement time of 50 seconds.

The signal-to-noise ratio is reduced by collecting large amounts of data using a high speed data acquisition system (e.g. NI-cDAQ or NI-cRIO with LabVIEW® FPGA and real time processing data acquisition systems) and subsequent averaging to ascertain the value measured at a specific position.

In addition, in the absence of motion interruption (for the continuous mode) and using fast polarization switching to measure TE and TM modes almost simultaneously, one can significantly reduce drift in the oil layer region in the measurement cell and/or other spurious mechanical noise.

Example configurations of the system utilize a light source capable of emitting different wavelengths of polarized light. The use of multiple wavelengths, including a blue laser light of wavelength 405 nm, enhances the spatial resolution from approximately 1 um (when using a 633 nm laser) to approximately 500 nm (using the 405 nm laser). Also, due to the improvements in spatial resolution and spot size, the blue laser allows for the measurement of the index and stress profile closer to the surface of sample, which is not possible with a red laser system. This also allows for a better post-processing of the data and improvements on the extrapolation of the stress to the sample surface.

Using a high-speed piezoelectric stage and a high-speed ferroelectric crystal polarization control and acquisition allows for the typical low frequency (e.g. <500 Hz) noise (for e.g. due to vibration of floor, noise due to air conditioning) to be readily filtered out. Also, the shorter measurement times reduce thermal noise effects.

Finally, the systems and methods allow for determining stress-based characteristics at the surface region of the sample, as explained below.

An embodiment of the disclosure is directed to a RNF measurement system used to measure at least one stress-based characteristic of a sample, comprising: a) a signal-generation section that generates a polarization-switched (PS) detector and reference signals SD and SR having a PS frequency representative of switching a measurement light beam between a transverse electric (TE) polarization and a transverse magnetic (TM) polarization; b) a signal-processing section in electrical communication with the signal-generation section and configured to receive and parallel process the PS detector and reference signals, the signal-processing section comprising: i) a gain adjuster configured to receive the PS detector and reference signals SD and SR and perform a gain adjustment to define gain-adjusted PS detector and reference signals SD' and SR'; ii) a digital input/output (I/O) card configured to generate a digital control signal S5 that the defines the PS frequency; iii) an analog input card electrically connected to the gain adjuster and the digital I/O card and configured to receive the gain-adjusted PS detector and reference signals SD' and SR' and the digital control signal S5 and use the digital control signal to synchronize the PS gain-adjusted detector and reference signals to define PS gain-adjusted synchronized detector and reference signals SD" and SR" each having respective steady-state portions SSD" and SSR"; and iv) a computer/controller configured to: receive the PS gain-adjusted synchronized detector and reference signals SSD" and SSR" and using the steady-state portions SSD" and SSR" of these signals to define a measurement signal SN=SSD"/SSR"; and calculate the at least one stress-based characteristic using the measurement signal SN.

Another embodiment of the disclosure is directed to a method of measuring at least one stress-based characteristic of a sample having stress-induced characteristics using a refracted near-field (RNF) measurement system, comprising: generating polarization-switched (PS) detector and reference signals SD and SR having a PS frequency representative of switching a measurement light beam between a transverse electric (TE) polarization and a transverse magnetic (TM) polarization by detecting PS detector and reference optical signals having the PS frequency as defined by a polarization switch controlled by a digital control signal; performing a gain adjustment on the PS detector and reference signals SD and SR to define gain-adjusted detector and reference signals SD' and SR'; using the digital control signal to synchronize the gain-adjusted PS detector and reference signals SD' and SR' to define gain-adjusted synchronized PS detector and reference signals SD" and SR" each having respective steady-state portions SSD" and SSR"; using the steady-state portions SSD" and SSR" of these signals to define a measurement signal SN=SSD"/SSR"; and calculating the at least one stress-based characteristic using the measurement signal Additional features and advantages will be set forth in the Detailed Description that follows and in part will be apparent to those skilled in the art from the description or recognized by practicing the embodiments as described in the written description, the claims thereof and the appended drawings.

It is to be understood that both the foregoing general description and the following Detailed Description are merely exemplary and are intended to provide an overview or framework for understanding the nature and character of the claims.

BRIEF DESCRIPTION OF THE DRAWINGS

The accompanying drawings are included to provide a further understanding and are incorporated in and constitute a part of this specification. The drawings illustrate one or more embodiment(s), and together with the Detailed Description explain the principles and operation of the various embodiments. As such, the disclosure will become more fully understood from the following Detailed Description, taken in conjunction with the accompanying Figures, in which:

FIG. 2A is a close-up, front-on view of an example confocal aperture.

FIGS. 2B and 2C are close-up, front-on views of examples of the first and second sectorial aperture stops, respectively.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute a part of this Detailed Description.

The entire disclosure of any publication or patent document mentioned herein is incorporated by reference.

Cartesian coordinates are shown in some of the Figures for the sake of reference and are not intended to be limiting as to direction or orientation.

The acronym "PS" as used below can stand for either "polarization switched" or "polarization switching," depending on the context of the discussion.

The acronym "DAQ" stands for "data acquisition," while the acronym cDAQ stands for "compact data acquisition."

The acronym "RIO" stands for "real-time input/output," while the acronym cRIO stands for "compact real-time input/output."

The acronym "I/O" stands for "input/output."

A number of the different components of the RNF system described below (e.g., the cDAQ and cRIO chassis and the digital and analog I/O cards) can be obtained from National Instruments Corporation, of Austin, Tex., which is referred to hereinafter as "National Instruments," and is also abbreviated as "NI."

Generalized RNF Measurement System

Figure 1A:
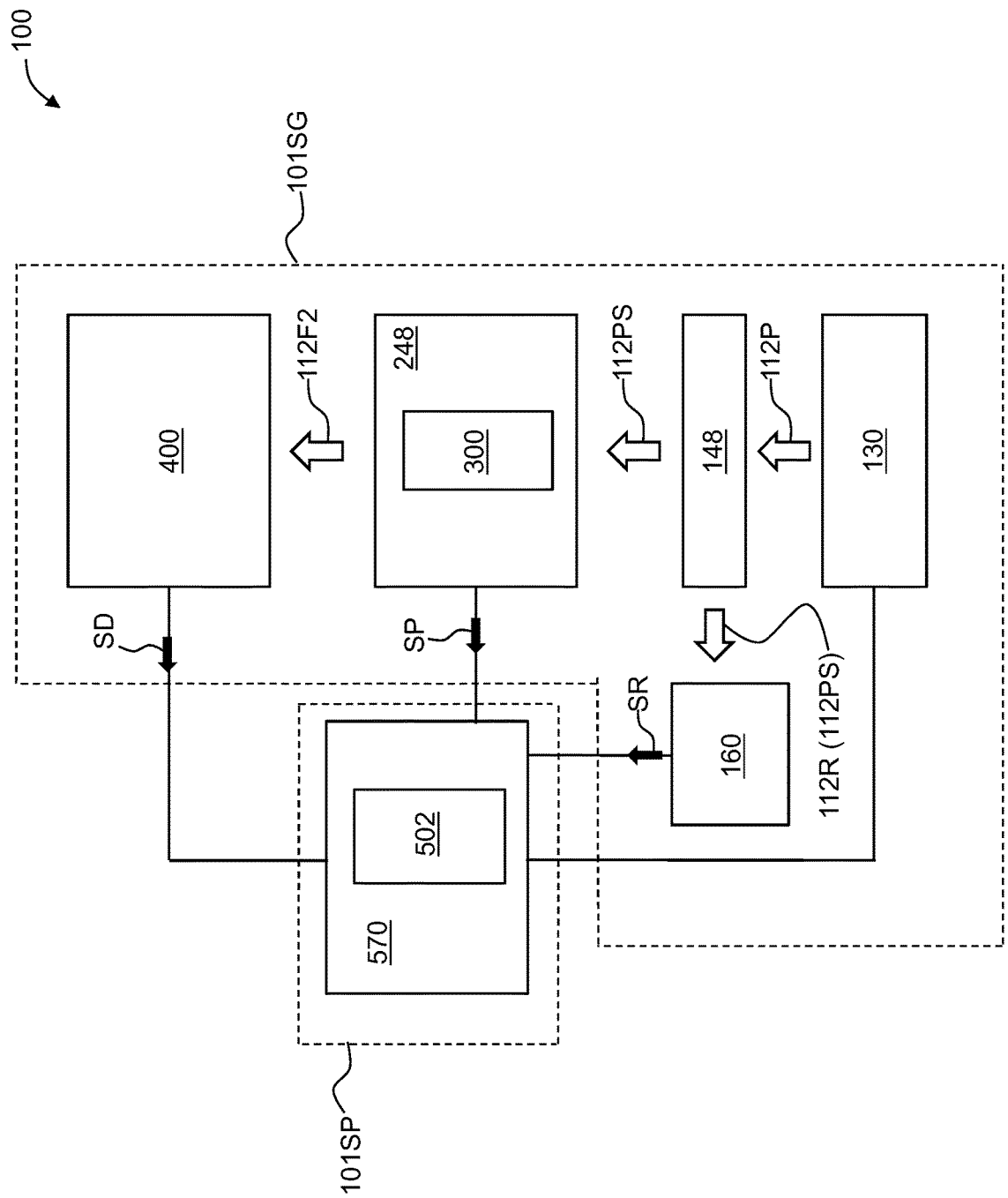
FIG. 1A is a generalized schematic diagram of an example RNF measurement system according to the disclosure.

FIG. 1A is a generalized schematic diagram of an example RNF measurement system ("system") 100 according to the disclosure. The system 100 is configured to measure one or more stress-based characteristics of a glass-based sample ("sample") 300. The stress-based characteristics can include refractive index profiles for orthogonal polarizations of light, a birefringence profile and a stress profile. All three of these profile characteristics are related.

The system 100 comprises a light-source system 130, a polarization switching system 148, a reference detector system 160, a sample positioning system 248 that positions the sample 300, and a signal detector system 400 operably arranged as shown. These components constitute a signal-generation section 101SG of the system 100.

The system 100 also includes a signal control and processing system 570. The signal control and processing system 570 includes an input/output (I/O) controller 502 configured to output control signals, receive inputted signals (e.g., reference and detector signals SR and SD, as described below) and generally control the processing of the various signals associated with the operation of system 100. The signal control and processing system 570 constitutes a signal-processing section 101SP of the system 100, wherein the signal-processing section is operably arranged relative to the signal-generation section 101SG and is in electrical communication therewith, and is configured to parallel process the detector and reference signals as described below.

In the general and overall operation of system 100, the light-source system 130 generates a polarized light beam 112P. The polarized light beam 112P is rapidly polarization-switched by the polarization switching system 148 to switch the polarization of the polarized light beam back and forth from a transverse electric (TE) polarization to a transverse magnetic (TM) polarization to form a polarization-switched light beam 112PS. A portion of the polarization-switched light beam 112PS is sent to the reference detector system 160, which generates a reference photodetector signal SR that is sent to the signal control and processing system 570. The other portion of the polarization-switched light beam 112PS is sent to the sample positioning system 248, which movably supports a glass-based sample ("sample") 300 to be measured.

Information about the position of the sample 300 relative to polarization-switched light beam 112PS or other reference is provided to the signal control and processing system 570 via a position signal SP. The portion of the polarization-switched light beam 112PS that interacts with the sample 300 and that proceeds to the signal detector system 400 is denoted 112F2 for reasons explained below. The system 100 includes a number of different apertures that are not shown in FIG. 1A for ease of description and illustration, but are described below.

The light beam 112F2 is received by the signal detector system 400, which forms therefrom a detector signal SD, which is sent to the signal control and processing system 570. As noted above, the I/O controller 502 controls the processing of the various signals associated with the system 100. The signal control and processing system 570 is also configured to calculate at least one stress-based characteristic of the sample based on the reference and detector signals SR and SD (or more specifically, based on processed versions of these signals), as described below.

Detailed Description of the RNF Measurement System

Figure 1B:
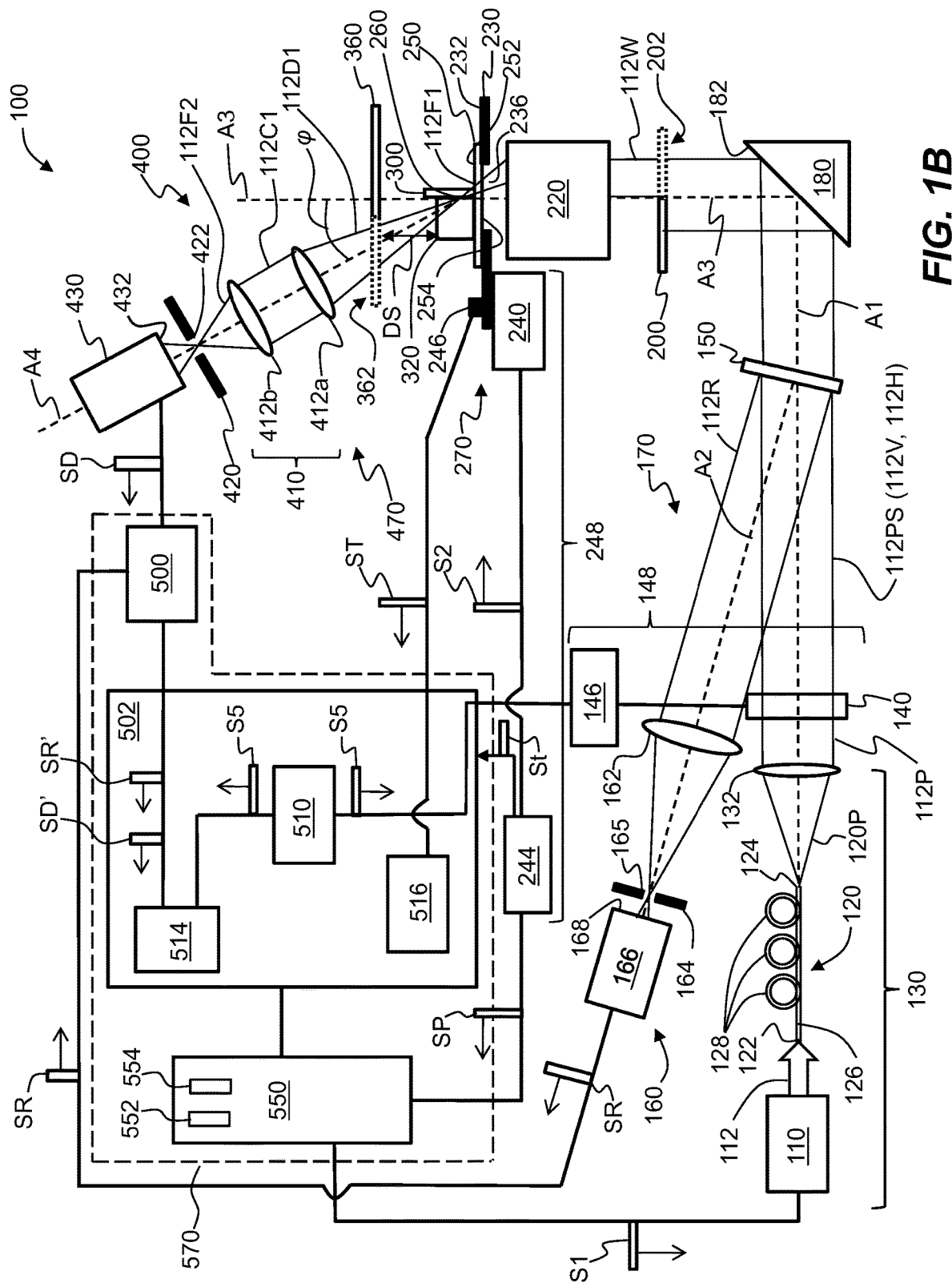
FIG. 1B is a detailed schematic diagram of an example RNF measurement system of FIG. 1A.

FIG. 1B is a more detailed schematic diagram of the system 100 of FIG. 1A. With reference to FIG. 1B, the light-source system 130 of the system 100 includes a light source 110 that emits a light beam 112 along a first optical axis A1 that runs in a first direction. An example light source 110 is a single-mode, fiber pig-tailed laser operating at a nominal wavelength of 405 nm. This is a "blue" wavelength and is substantially shorter than the prior-art red wavelengths (e.g., 633 nm) and allows for a substantially higher measurement resolution. In an example, the light source 110 can emit light of multiple wavelengths, including blue and red wavelengths.

The light-source system 130 also includes a polarization controller 120 having an input end 122 and an output end 124. The light source 110 is optically coupled to the input end 122 of the polarization controller 120. The polarization controller 120 receives the light beam 112 from the light source 110 and outputs a polarized light beam 120P. An example polarization controller 120 is fiber based and includes a section of single-mode optical fiber 126 that is wrapped around fiber paddles 128 that induce stress birefringence into the optical fiber to create the desired output polarization, such as TE polarization (i.e., vertical polarization) or TM polarization (i.e., horizontal polarization).

The light-source system 130 also includes a collimating lens 132. The polarization controller 120 is optically coupled at its output end 124 to the collimating lens 132. The collimating lens 132 is configured to receive the divergent polarized light beam 120P emitted by the single-mode optical fiber 126 of the polarization controller 120 and forms a collimated, free-space polarized light beam 112P, which in an example has a generally circular cross-sectional shape. The collimating lens 132 can include one or more lens elements or other types of optical elements, such as reflective elements.

The system 100 also includes the aforementioned polarization switching system 148, which comprises a polarization switch 140 located downstream of the collimating lens 132 along axis A1 so that it receives the collimated polarized light beam 112P. The polarization switching system 148 also includes a polarization switch controller, which is operably connected to the polarization switch 140. In an example, the polarization switch 140 is in the form of a ferroelectric liquid crystal (FLC) polarization rotator, which in an example operates at a switching rate (PS frequency) of as high as 5 KHz, which corresponds to a measurement time of 0.2 ms. In the discussion below, the polarization switch 140 is also referred to as the FLC polarization switch.

The polarization switch 140 is driven by polarization-switch controller 146 to switch the polarization state of polarized light beam 112P back and forth between TE and TM polarizations (i.e., vertical and horizontal polarizations) 112V and 112H. The polarized light beam 112P is thus converted to the polarization-switched light beam 112PS. An example switching time of the polarization switch 140 is between 1 millisecond and 100 milliseconds, with an exemplary switching time being about 1 millisecond. In an example, the polarized light beam 112P leaves the polarization controller 120 as either TE or TM polarized light, and polarization switch 140 switches the polarized light beam 112P to the other polarization when activated, i.e., to form the polarization-switched light beam 112PS.

The system 100 further includes along axis A1 and downstream of the polarization switch 140 a beam-splitting element 150. An example beam-splitting element 150 is very thin, e.g., an uncoated pellicle. The beam-splitting element 150 is configured to reflect a relatively small portion as a reference light beam 112R of the polarization-switched light beam 112PS along a second optical axis A2. In an example, the reference light beam 112R is up to 50% of the polarization-switched light beam 112PS, but in other examples is less than 20% or less than 10% of the polarization-switched light beam, with 8% being an exemplary amount. In an example, the beam-splitting element 150 comprises a pellicle beam splitter.

In an example, second optical axis A2 makes a relatively shallow angle with first optical axis A1, i.e., the polarization-switched light beam 112PS is near-normally incident upon the beam-splitting element 150. This helps to ensure that the reflection of the TE and TM polarization states from the beam-splitting element 150 is about the same. This is because the difference in reflectance of TM and TE light changes strongly with increasing angle. A thin beam-splitting element 150 has the benefit that ghost reflection offsets from multiple reflections between its two surfaces are negligible.

A reference detector system 160 is arranged along the second optical axis A2. The reference detector system 160 includes, in order along the second optical axis: a focusing lens 162 having a focal length f1, a confocal aperture 164 arranged a distance f1 away from the focusing lens, and a reference photodetector 166 that has a photosensitive surface 168. The reference detector system 160 is configured to receive and detect the (polarization-switched) reference light beam 112R that in the example system of FIG. 1B is reflected by the beam-splitting element 150 to travel along the second optical axis A2. In an example, the focusing lens 162 is achromatic. The reference photodetector 166 generates a reference signal SR representative of the polarization-switched reference light beam in response to receiving the polarization-switched reference light beam 112R.

Figure 1C:
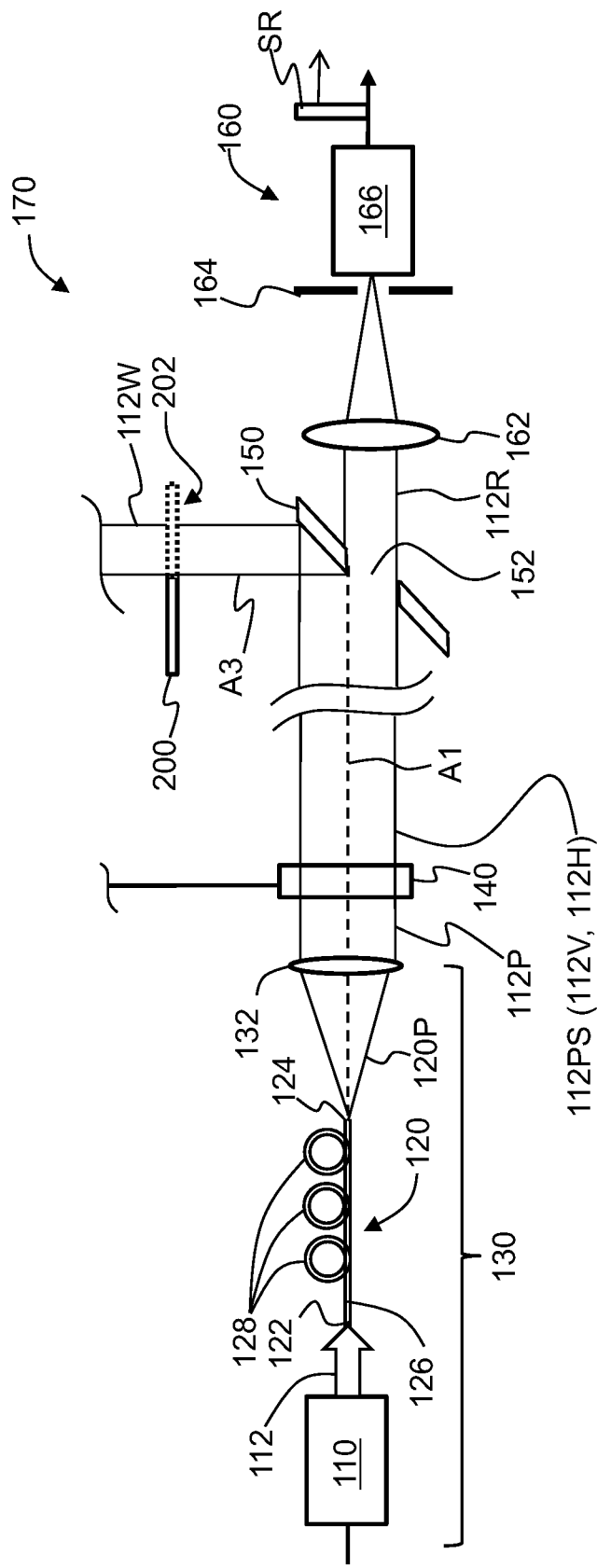
FIG. 1C is a close-up view of the reference arm of the RNF measurement system of FIG. 1B, illustrating another example configuration of this part of the system wherein the reference portion of the polarization-switched light beam is transmitted through an aperture in the beam-splitting element to define the reference light beam, thereby avoiding having to detect a reflected reference light beam.

FIG. 1C is a close-up view of the reference arm 170 and the reference detector system 160 therein illustrating an alternate embodiment of the system 100 and in particular the reference detector system. In the alternate embodiment, the light-turning member 180 is omitted and beam-splitting element 150 is provided with an aperture 152 through which a portion of the polarization-switched light beam 112PS can pass as a transmitted reference light beam 112R that travels along the axis A1 rather than as a reflected reference light beam that travels along the axis A2, which is no longer present in the system 100. The focusing lens 162, the confocal aperture 164 and the reference photodetector 166 are disposed to received and process the transmitted reference light beam 112R and generate the reference signal SR. The reference signal SR from the reference photodetector 166 is then processed in the same manner as for the system configuration of FIG. 1B. In the embodiment of FIG. 1C, the reference light beam 112R, which represents a reference optical signal, travels along the first axis A1, and the reference light beam (reference optical signal) does not undergo a reflection that changes the first direction of the first optical axis. This has the advantage of eliminating reflection-induced changes in polarization, which can lead to errors in the measurement of a stress-based characteristic of the sample.

FIG. 2A is a close-up, front-on view of an example confocal aperture 164. The confocal aperture 164 has a small on-axis opening 165. The second optical axis A2 and reference detector system 160 define a reference arm 170 of system 100.

With reference again to FIG. 1B, the example configuration of system 100 therein also includes a light-turning member 180 arranged downstream of the beam-splitting element 150 along the first optical axis A1. The light-turning member 180 defines a third optical axis A3 that in an example makes a right angle with first optical axis A1. An example light-turning member 180 is a mirror having a reflecting surface 182. The light-turning member 180 serves to reflect the polarization-switched light beam 112PS to travel along the third optical axis A3.

The system 100 also includes a first sectorial aperture stop 200 disposed downstream of the light-turning member 180 and along third optical axis A3. FIG. 2B is a close-up, front-on view of an example of the first sectorial aperture stop 200. The first sectorial aperture stop 200 is defined by an off-axis first opening 202 that is wedge-shaped (see FIG. 2B). The first opening 202 is configured to form from the polarization-switched light beam 112PS a wedged-shaped off-axis polarization-switched light beam 112W. The first opening 202 is configured to pass only the portion of the polarization-switched light beam 112PS that has the potential to follow a trajectory to a signal photodetector 430 via a first-pass refraction through the measurement region and out of the top surface of a reference block 320 (the signal photodetector 430 and the reference block 320 of the measurement region are introduced and discussed below).

Any portion of the polarization-switched light beam 112PS that would otherwise not refract out of a top 322 of reference block 320 on the first pass must be blocked by the opaque regions defining the wedge-shaped first opening 202. As shown in FIG. 2B, the example wedge-shaped first opening 202 has an apex 204 an an associated an angle η that in an example is adjustable, e.g., between 0° and 90°, so that the cross-sectional shape of the transmitted wedge-shaped polarized light beam 112W can be adjusted. The apex 204 of wedge-shaped first opening 202 is located along third optical axis A3.

The system 100 also includes, along third optical axis A3 and downstream of first sectorial aperture stop 200, an objective lens 220 and a movable support platform 230 that is supported by a positioning stage 240 that is movable in the X, Y and Z directions (i.e., three dimensions). The positioning stage 240 is operably connected to a stage controller 244. Thus, positioning stage 240 is operable to move the support platform in three dimensions. In an example, the positioning stage 240 comprises a precision friction-driven piezoelectric-based motion stage. The stage controller 244 and the positioning stage constitute the sample positioning system 248.

An example objective lens 220 is a microscope objective that is centered to be co-axial with third optical axis A3 and the apex 204 of the first sectorial aperture stop 200. The support platform 230 has an upper surface 232 that supports a coverslip 250 having top and bottom surfaces 252 and 254. The support platform 230 has an aperture 236 through which the polarization-switched light beam 112PS passing through first sectorial aperture stop 200 as the wedge-shaped light beam 112W can pass and then pass through coverslip 250. The objective lens 220 is corrected for the presence of coverslip 250.

Figure 3B:
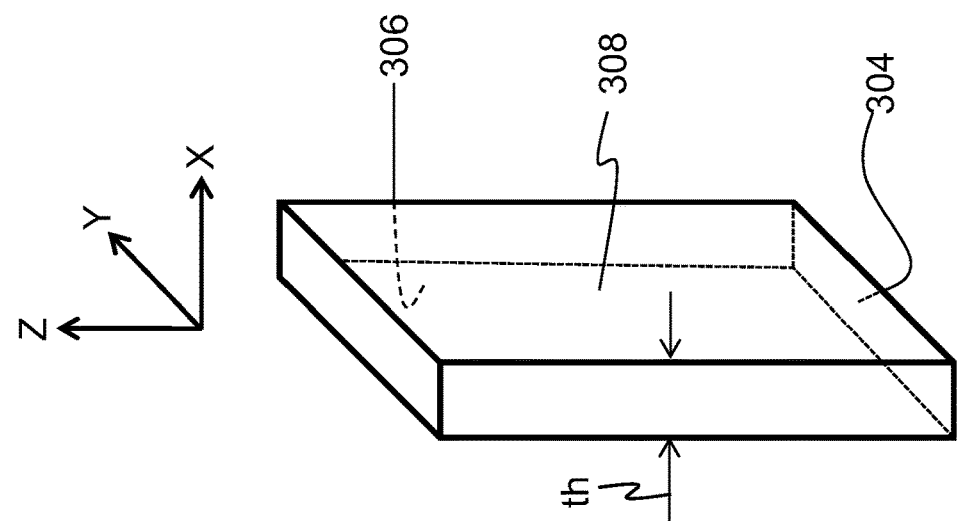
FIG. 3B is an elevated view of the sample, wherein the edge surface (304) is the input side, i.e., the side that is in contact with the coverslip and index-matching oil, and wherein the surface (306) is in contact with the reference block (see FIG. 3A).
Figure 3A:
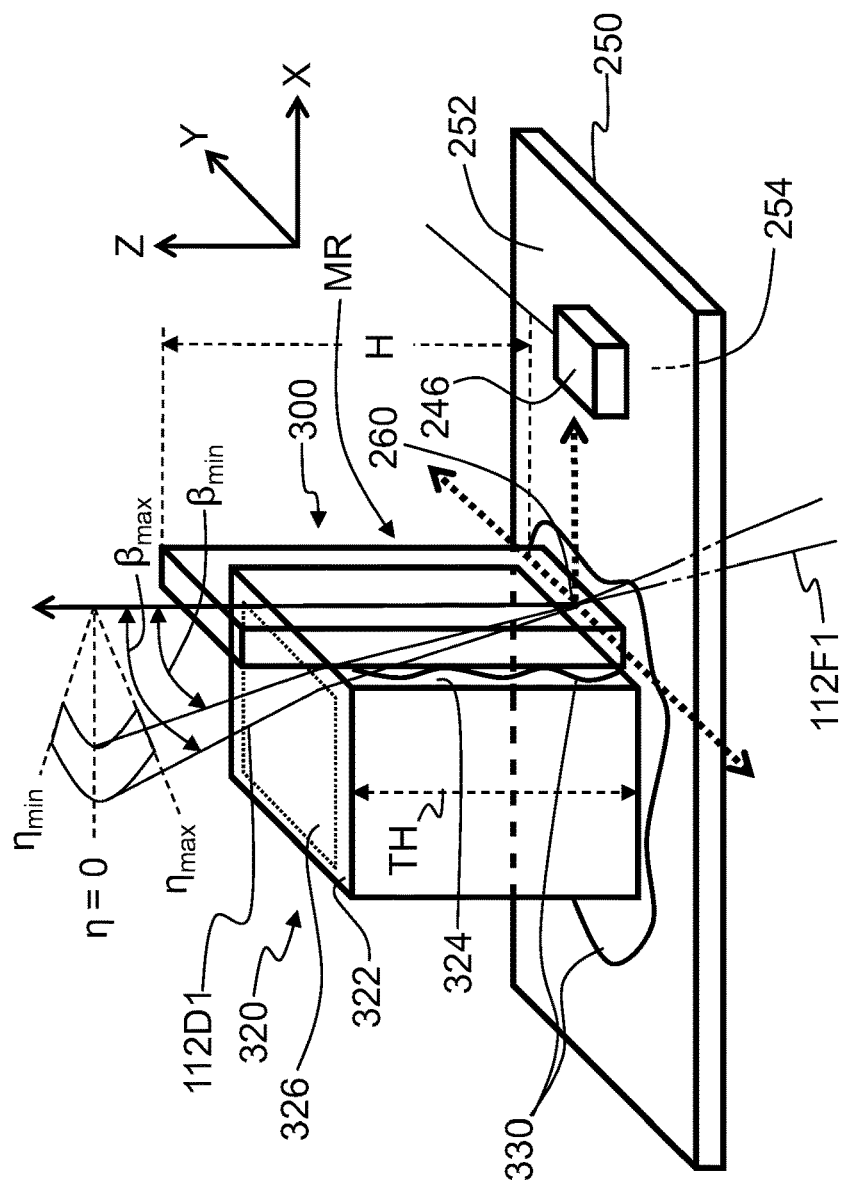
FIG. 3A is an elevated view of the reference block and sample as arranged atop the coverslip in the RNF measurement system of FIG. 1B.

The system 100 also includes a sample 300. The sample 300 is supported on coverslip 250 along with reference block 320. FIG. 3A is a close-up, elevated view of sample 300 and reference block 320 disposed on top surface 252 of coverslip 250. FIG. 3B is a close-up, elevated view of just the sample 300. The sample 300 has an edge surface 304, a front surface 306 and a back surface 308. The edge surface 304 confronts the top surface 252 of coverslip 250. The sample 300, the reference block 320 and the cover slip reside within a measurement region MR.

The reference block 320 has the aforementioned top surface 322 and a front surface 324. The reference block 320 and the sample 300 are arranged so that the front surface 324 of the reference block 320 confronts the front surface 306 of the sample. The stress-based characteristic to be measured has a gradient at least along the X-direction.

The edge surface 304 is measured in the X-Y plane. A scanning measurement of the edge surface 304 can be made as a function of position. The sample 300 has a thickness th in the X-direction that in an example can be 2 mm or less. In an example, the edge surface 304 is processed, e.g., cleaved and/or polished, to expose the depth of the stress profile extending along the edge surface 304 from between the front surface 306 and the back surface 308.

Figure 4B:
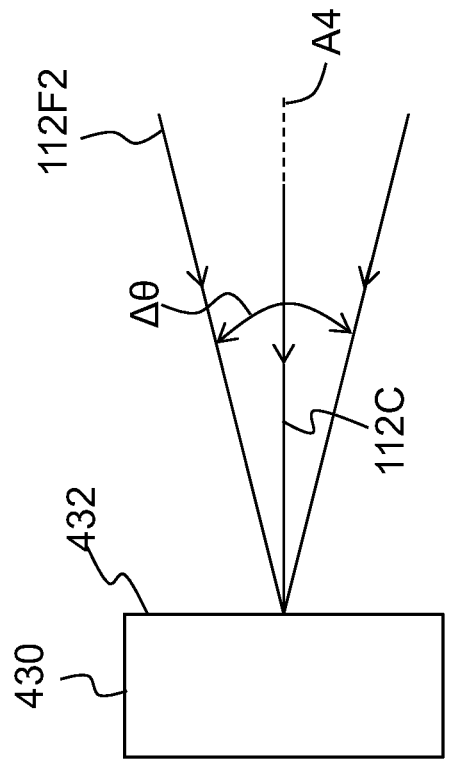
FIG. 4B is a close-up side view of the signal photodetector showing the focused polarization-switched light beam incident on the signal photodetector with its central ray at normal incidence, and showing the range of angles $\Delta\theta$ in the focused polarization-switched light beams.
Figure 4A:
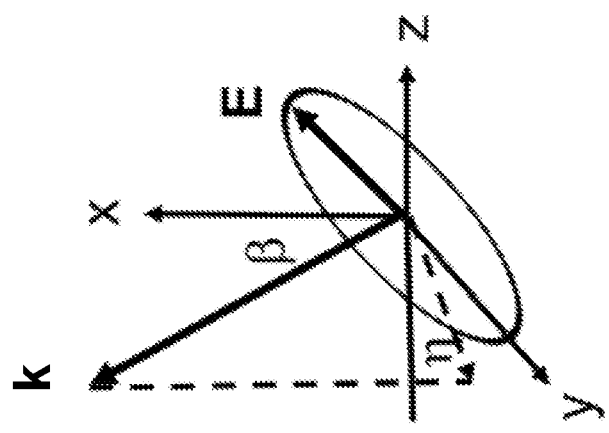
FIG. 4A is a schematic diagram of an example RNF measurement configuration showing a polarization state of the electric field vector E of one of the rays in the section of light that propagates along a propagation direction k (i.e., the k vector, denoted k) and also showing the polar angle $\beta$ and azimuthal angle $\eta$.

Single or multiple scans of the sample (see FIGS. 12A, 12B, introduced and discussed below) can be made at a variety of positions over distances of several millimeters. The polar angle $\beta$ and the azimuthal angle $\eta$ associated with a polarization-switched diverging light beam 112D1 exiting the sample 300 are shown in FIG. 3A, with example limits $\beta_{min}$, $\beta_{max}$ and $\eta_{min}$, $\eta_{max}$. The reference block 320 has a thickness TH in the z-direction. An example range for the thickness TH is between 5 mm and 20 mm, with 8 mm being an exemplary thickness within the range. FIG. 4A is a schematic diagram of an example measurement configuration showing the polarization state of the electrical field vector E of one of the rays in the section of wedge-shaped light beam 112W that propagates along a propagation direction k (i.e., the k vector) and also showing the polar angle $\beta$ and azimuthal angle $\eta$.

In an example embodiment, an index-matching oil 330 is used to ensure low-reflection optical coupling between the coverslip 250, the edge surface 304 of the sample 300, the front surface 306 of the sample and the front surface 324 of the reference block 320. The coverslip bottom surface 254 and the reference block top surface 322 may each be optionally coated with a polarization-independent and angularly independent anti-reflection (AR) coating 326 (shown with a dotted-line boundary in FIG. 3A) to minimize the reflectance variations for polarization and ranges of incident angles.

A temperature sensor 246 (e.g., a thermocouple) is in thermal communication with the positioning stage 240 and generates a temperature signal ST representative of the local temperature. The temperature signal ST is provided to the I/O controller 502, and in particular to a temperature input module 516 therein, such as the NI-9210 temperature input module, available from National Instruments. The temperature sensor 246 is used to precisely measure the ambient (local) temperature of the sample 300 and index-matching oil 330 because the indices of refraction of the materials of these components are temperature sensitive and can affect the measurement. In an example, the main computer-controller 550 (introduced and discussed below) includes temperature-based index of refraction data for the sample 300 and index-matching oil 330 for use in calculating one or more of the stress-based characteristics of the sample based on the temperature dependency of the refractive indices.

The polarization-switched light beam 112PS passes off-axis through the wedge-shaped first opening 202 of first sectorial aperture stop 200 and the resultant wedge-shaped polarization-switched light beam 112W enters the objective lens 220, which is centered on the third optical axis A3. The width of the polarization-switched light beam 112PS is such that it overfills the input clear aperture (not shown) of the objective lens 220. This overfilling ensures that only the most intense and roughly uniform, substantially Gaussian center-portion of the polarization-switched light beam 112PS is focused onto the edge surface 304 of the sample 300 as a first focused light beam 112F1.

This overfilling also helps to reduce or eliminate any adverse diffractive effects from the outer circular portion of wedge-shaped first opening 202. Because polarization-switched light beam 112PS enters objective lens 220 from an off-axis position relative to third optical axis A3, the objective lens forms a polarization-switched, first focused light beam 112F1.

The system 100 also includes a fourth optical axis A4 that intersects the third optical axis A3 at a focus position of the objective lens 220, with the focus position being located on the edge surface 304 of the sample 300. A signal detector system 400 is operably arranged along fourth optical axis A4. An example signal detector system 400 includes, in order along fourth optical axis A4, a relay optical system 410, a confocal variable aperture 420 with an on-axis opening 422, and the signal photodetector 430, which has a photosensitive surface 432. In an example, the relay optical system 410 is achromatic. An example achromatic relay optical system 410 as shown in FIG. 1B includes a pair of lens elements 412a and 412b. In an example, each lens element 412a and 412b has a focal length f2 (e.g., f2=80 mm) and includes antireflection coatings. An example diameter (clear aperture) of lens elements 412a and 412b is about 2 inches. FIG. 4B shows an example where the signal photodetector 430 is arranged along fourth optical axis A4 so that a central ray 112C of a second focused light beam 112F2 is incident nearly perpendicularly to the signal photodetector for all incident angles $\theta$ in the range $\Delta\theta$ of the focused light beam.

In the example two-lens embodiment of relay optical system 410, the first lens element 412a is located a focal-length f2 away from where the axes A4, A3, focus 260 (see FIG. 3A) and the edge surface 304 intersect. The first focused light beam is focused down to the focus 260 at the edge surface 304 and then diverges beyond the focus as a diverging light beam 112D1. The first lens element 412a receives and collimates the diverging light beam 112D1 to form a collimated light beam 112C1 without vignetting. The second lens element 412b is arranged so that it receives collimated light beam 112C1 and re-focuses the beam to form a second focused light beam 112F2. The second focused light beam 112F2 passes through confocal variable aperture 420 and is received and detected by signal photodetector 430. In response, signal photodetector 430 generates the aforementioned (polarization-switched) detector signal SD. In an example, signal photodetector 430 is placed slightly beyond the focusing point of the second lens element 412b. Note that the various light beams described above are all polarization-switched light beams except for the initial polarized light beam 112P that is upstream of the polarization switch 140.

The system 100 also includes a second sectorial aperture stop 360 downstream of reference block 320 and sample 300 and along third optical axis A3. FIG. 2C is a close-up, front-on view of an example of the second sectorial aperture stop 360. The second sectorial aperture stop 360 includes a second opening 362 that is offset from the center of the stop and whose azimuthal pass angle range may be fixed or manually adjustable. An example second sectorial aperture stop 360 has an arcuate shape. The fourth axis A4 passes nominally through the center of the arcuate-shaped second opening 362.

In an example, second sectorial aperture stop 360 includes two semicircular movable portions 364 and a central disk 366. A central fastening member 368 secures the semicircular movable portions 364 so that they can rotate to open and close second opening 362 (as indicated by the bold arrows) while keeping inside edges 369 of the semicircular movable portions 364 directed radially to the third optical axis A3 of the beam at all angular positions.

The first sectorial aperture stop 200, the objective lens 220, the movable support platform 230, the coverslip 250, the positioning stage 240, and the second sectorial aperture stop 360 constitute a scanning optical system 270.

In an example, the second opening 362 of the second sectorial aperture stop 360 has the aforementioned arcuate shape with an associated nominal azimuthal pass-band angle of 36° (+/−18°) and a minimum polar pass angle $\beta_{min}$ of 26°. In an example, the second opening 362 of the second sectorial aperture stop 360 has a smaller area than the first opening 202 of the first sectorial aperture stop 200. This configuration serves to block diffracted light that arises from the interaction of the polarization-switched light beam 112PS with the edges of the wedge-shaped first opening 202 of the first sectorial aperture stop 200. Such diffracted light can adversely impact the measurement. The polarization-switched first focused light beam 112F1 that leaves objective lens 220 and travels along fourth optical axis A4 passes through aperture 236 of movable support platform 230, through coverslip 250 and reaches edge surface 304 of sample 300. The refractive index profile(s) that is (are) to be measured lie(s) along the plane of edge surface 304.

After the focus 260, the polarization-switched first focused light beam 112F1 diverges and continues through front surface 324 of reference block 320 and exits top surface 322 as a diverging light beam 112D1. A portion of this polarization-switched diverging light beam 112D1 then passes through the second opening 362 of the second sectorial aperture stop 360.

The portion of the diverging light beam 112D1 propagating at polar angles less than $\beta_{min}$ is blocked by the second sectorial aperture stop 360 while the portion propagating at angles greater than $\beta_{min}$ is transmitted. Thus, if the refractive index at the edge surface 304 decreases, then the refraction angle of the rays from diverging light beam 112D1 increases and light that was otherwise blocked now exceeds the minimum polar angle $\beta_{min}$ and is ultimately detected. This causes the optical power at the signal photodetector 430 to increase. Conversely, if the refractive index at the edge surface 304 increases, then the refraction angle of the rays from the polarization-switched first focused light beam 112F1 decreases and less optical power manages to exceed the minimum polar angle $\beta_{min}$ and is blocked by the second sectorial aperture stop 360. This causes the optical power at the signal photodetector 430 to decrease.

The second sectorial aperture stop 360 is arranged at a distance DS from the top surface 322 of reference block 320. In an example, the distance DS is in the range from 8.5 mm to 37.5 mm. However, the distance DS can be such that a sample 300 having a height H of up to 3 inches can be accommodated between coverslip 250 and second sectorial aperture stop 360, where the limitation is defined by the instance of the second sectorial aperture stop 360 intersecting the first lens element 412a.

The confocal variable aperture 420, which can be an adjustable iris, is disposed at the focal point of the relay optical system 410 (e.g., a distance f2 behind second lens element 412b) to create a confocal signal detection arrangement. Note that the reference detector system 160 also has a confocal detection arrangement, but with only one focusing lens 162 because the reference light beam 112R from the beam-splitting element 150 is already collimated. The signal detector system 400 and the fourth optical axis A4 define a signal arm 470 of the system 100.

In an example, the on-axis opening 165 of the confocal aperture 164 can be stopped down to approximately 1 mm in diameter or even smaller. The confocal detection arrangement for the signal detector system 400, combined with the large offset distance (e.g., about 200 mm) of the signal photodetector 430 from the measurement region MR serves to prevent the majority of any undesirable scattered and reflected light from the measurement region from reaching the reference photodetector 166 and the signal photodetector 430. This serves to eliminate measurement errors owing to scattered light and/or reflected light.

A problem common to all photodetectors is that the efficiency of the photodetection varies over the face of the photodetector. Generally, the larger the photodetector is, the more the detection uniformity can vary across the face. In high-quality photodetectors, variations in detection uniformity over 1 $cm^2$ can be approximately ±2%. These uniformity variations impart an error to the measured optical power versus refracted angle and therefore contribute to error in the scaling of the measured index of refraction.

In principle, these kinds of inherent detection errors can be reduced or eliminated through a calibration process. This calibration step can include scanning a sample of a known refractive index profile and then re-mapping the measured sample data to improve the accuracy. However, it would be most desirable to avoid this added step by keeping the illuminated area of the given detector as small as possible.

General Description of the Signal Control and Processing System

With reference again to FIG. 1B, the system 100 includes a gain adjuster 500 that is electrically connected to the positioning stage 240, signal photodetector 430 and the reference photodetector 166. In an example, the gain adjuster 500 comprises a dual-channel power meter. The gain adjuster 500 is also electrically connected to an input/output (I/O) controller 502. The I/O controller 502 comprises a master-trigger controller 510 electrically connected to the polarization-switch controller 146 and to the analog input card 514. In an example, the I/O controller 502 comprises a chassis, such as a cDAQ or cRIO chassis, available from National Instruments. The particular chassis used depends in part on the particular data collection method (mode) employed (e.g., pulsed or continuous modes), as discussed below. In an example, the master-trigger controller 510 comprises a digital output card, as described below, in which case the master-trigger controller 510 is also referred as the digital output card 510.

The system 100 can also include a main computer-controller 550 that is operably connected to the I/O controller 502. In an example, main computer-controller 550 includes a processor 552 and a memory unit ("memory") 554 configured to execute instructions stored in firmware and/or software, including calculations and signal-processing instructions for carrying out the measurements disclosed herein. In examples, the terms "controller" and "computer" are interchangeable The main computer-controller 550 is programmable (e.g., using instructions embodied in a non-transitory computer-readable medium, i.e., software) to perform the functions described herein, including the operation of the system 100 and carrying out calculations for estimating or otherwise measuring of the aforementioned at least one stress-based characteristic of the sample 300. As used herein, the term "computer" is not limited to just those integrated circuits referred to in the art as computers but broadly refers to computers, processors, microcontrollers, microcomputers, programmable logic controllers, application-specific integrated circuits and other programmable circuits, and these terms are used interchangeably herein. In an example, the I/O controller 502 can be considered a part of the main computer-controller 550.

The software may implement or aid in the performance of the operations of the system 100 as disclosed herein. The software may be operably installed in the main computer-controller 550 and in particular in the processor 552 and the memory 554 and also in the I/O controller 502. Software functionalities may involve programming, including executable code, and such functionalities may be used to implement the methods disclosed herein. Such software code is executable by the main computer-controller 550, e.g., by the processor 552 therein. In an example, the I/O controller 502 includes a field-programmable gate array (FPGA) programmed with data-processing software, such as labVIEW® systems engineering software from National Instruments.

The main computer-controller 550, the I/O controller 502 and the gain adjuster 500 constitute an example of the signal control and processing system 570, as indicated by the dashed-line box and as shown in FIG. 1A.

General Operation of the RNF Measurement System

The general operation of the system 100 is first described. A more detailed description of the data collection and processing steps is then provided.

With continuing reference to FIGS. 1A and 1B, in an example, light source 110 emits a continuous-wave (CW) light beam 112. However, in another example, the light beam 112 may be pulsed and controlled during the measurement of the sample 300 using system 100. In one example, light source 110 is activated by the main computer-controller 550 by sending a light-source control signal S1 to the light source to cause the light source to emit the light beam 112. Alternatively, the light source 110 can be manually activated.

The stage controller 244 is configured to control the movement of the positioning stage 240 during the measurement process. In an example, the movement of the positioning stage 240 is used to scan the movable support platform 230 through the focused wedge-shaped polarized light beam 112W (i.e., the first focused light beam 112F1), thus moving the focus 260 across the edge surface 304 of sample 300.

The power measured by signal photodetector 430 is embodied in the detector signal SD and the power measured in the reference light beam 112R by reference photodetector 166 is embodied in the reference signal SR. The detector signal SD and the reference signal SR are sent to the gain adjuster 500, which adjusts the gain of each of these signals to define gain-adjusted detector and reference signals SR' and SD', which facilitate subsequent signal processing as described below.

The gain-adjusted detector and reference signals SD' and SR' are provided to the main computer-controller 550, which synchronizes these signals using the digital control signal (e.g., TTL signal) S5 to define synchronized gain-adjusted detector and reference signals SD" and SR". These signals are then used by the main computer-controller 550 to form a normalized or "measurement" signal SN (see FIG. 6) by dividing steady-state portions of the synchronized gain adjusted detector signal by corresponding (synchronized) steady-state portions of the synchronized gain-adjusted reference signal SSR", as described below (see FIG. 7). This normalizes out any temporal power variations from the light source 110, as well as any polarization-dependent transmittance differences through the polarization switch 140 and any other surfaces. The resulting normalized signal SN is referred to hereinafter as the measurement signal.

The measurement signal SN contains information about the refractive index profile for both the TE and TM polarizations by virtue of the reference and detector signals SR and SD being polarization-switched signals. The refractive index profile for each polarization is calculated by the main computer-controller 550 based on the data embodied in the measurement signal SN using techniques known in the art. As noted above, the main computer-controller 550 receives temperature signals ST that are used to establish or correct the values of the refractive indices of the sample 300 and index-matching oil 330 based on the measured local temperature.

In an example, the measurement scan of the sample 300 is extended outside of sample 300 to include two reference regions that have precisely known indices of refraction. It is desirable that these two reference regions consist of homogeneous, isotropic non-birefringent media. In an example, the two regions are a portion of the reference block 320 and a portion of index-matching oil 330. The indices of refraction of the two reference regions ($n_1$ and $n_2$) should be near to, but slightly different from, one another. Scaling factors M can be used to transform the measured power into the refractive index for each polarization state.

The scaling factors M are determined by the two-point calibration process of taking the ratio of the difference in refractive indices of the two reference scan regions to the difference in the optical power ratios (signal power $P_{1,sig}$/reference power $P_{2,ref}$) as measured when each polarization state is scanning through those reference regions. This is expressed by the following equation (EQ. 1):

$$M=(n_1-n_2)/(P_{1,sig}/P_{1,ref}-P_{2,sig}/P_{2,ref}). \quad [\text{EQ. 1}]$$

Each polarization state has a slightly different transmitted optical power when scanning through these reference regions, and thus the normalization of the refractive index to the normalized power should be carried out separately for each polarization state, leading to a different scaling factor ($M_{TE}$ and $M_{TM}$) for each profile. The difference in the TE and TM refractive index profiles $n_{TE}(x)$ and $n_{TM}(x)$ defines the amount of birefringence (profile) $B(x)=\Delta n(x)=n_{TM}(x)-n_{TE}(x)$ in the sample 300. The calculation of the stress (profile) $S(x)$ in the sample is related to the birefringence $B(x)$ through the stress-optic coefficient SOC via the relationship $S(x)=B(x)/SOC$.

In its most general form, the stress S and birefringence B are 3×3 tensors and are related to each other through a $4^{th}$-ranked stress-optic tensor. For samples 300 that have stress symmetry, there can be many degeneracies and zeros in the coefficients of the stress-optic tensor if the polarization of the measurement light that is incident upon the sample is carefully controlled. In some cases, certain non-zero coefficients of the stress-optic tensor are negligible when compared to others and can ignored. Thus, the otherwise intractable problem of measuring the stress profile $S(x)$ through birefringence measurements is made tractable because of geometrical symmetries and simplifications that can be made in the stress-optic tensor as it relates to the sample and optical method of interrogation.

In particular, in cases of stress symmetry in the sample 300 and with the wave propagation (k-vector) and polarizations properly oriented within principle planes of stress, many of the stress optic tensor components are either zero, very small and/or are degenerate. In that case, the stress optic tensor, when multiplied out with the electromagnetic field equations, will reduce to an expression that has a single stress coefficient number, namely the stress optic coefficient SOC.

The stress-optic coefficient SOC is unique for each glass composition. However, the magnitude for most glasses generally ranges from $2.5 \times 10^{-6}$ to $3.5 \times 10^{-6}$ birefringence refractive index units (RIU) per mega-Pascal (MPa). Table 1 below shows the achievable stress-measurement accuracy or resolution that is associated with various orders of birefringence accuracy or resolution, given a nominal stress-optic coefficient SOC of $3.0 \times 10^{-6}$ birefringence (RIU/MPa).

TABLE 1

| B (RIU) | S (MPa) |
|---|---|
| 0.001 | 333 |
| 0.0001 | 33.3 |
| 0.00001 | 3.33 |
| 0.000001 | 0.333 |

An advantage of system 100 is that it can use less precise positioning control of the sample 300 because there is no need to acquire TE and TM scans in series to measure the sample. The TE and TM measurements occur substantially simultaneously (i.e., within about 0.1 to 0.5 milliseconds of each other) and at the same location. Using the method of first measuring at one polarization state and then going back to measure at the other polarization state requires the use of a very precise and repeatable positioning method and apparatus.

Generally, piezoelectric positioners would limit the scan upper range to a maximum of 500 micrometers, which would not be useful for measuring many types of stress-strengthened glass products. Thermal drift and other time-dependent errors are also much larger if the two polarization scans are performed sequentially rather than simultaneously.

It has also been observed that integrating the measured optical power for a brief time interval (e.g., 0.5 ms for 1 KHz FLC switching frequency) for each polarization state at a given position leads to more noise in the birefringence and stress profiles rather than less as one might expect. This is attributable to the fact that integrating the power for each polarization state also generates a greater separation in time between the measurements of the signal powers of the two polarization states, which diminishes the common-mode rejection advantages of the measurement systems and methods disclosed herein.

The TE and TM polarized refracted light in the polarization-switched light beam 112PS that travels through the sample 300 is collected at very high temporal resolution (nearly simultaneously) with a negligible (thermal and thermomechanical) drift by using the aforementioned high-speed FLC polarization switch 140. As noted above, the FLC polarization switch 140 can modulate the state of polarization of light between TE and TM at very high speeds, e.g., up to 5 kHz. This generates a large amount of measurement data, which is received and processed downstream. The signal control and processing system 570 is configured to synchronize the generation of this measurement data as well as receive and process the large amount of measurement data, as described in greater detail below.

The reference signal SR can be measured using the first or second example configurations of the system 100 as shown in FIGS. 1B and 1C, respectively. In the first example configuration, the pellicle beam-splitting element 150 can be placed at near-normal incidence to the polarization-switched light beam 112PS, so that the reflected light that defines the reference light beam 112R is approximately of the same order of intensity for both polarization states. For the second example configuration of the system 100, there is no reflection of the polarization-switched light beam 112PS so that the state of polarization of the reference signal SR associated with the reference light beam 112R maintains a fixed TE/TM ratio without any change prior to being received by the reference photodetector 166.

In both example configurations of the system 100, the detector signal SD is normalized by the main computer-controller 550 using the detected reference signal SR and timing signals (as discussed below) to form the measurement signal SN as described above.

For planar samples 300, the system 100 measures the refracted light power in a sector of light (i.e., wedge-shaped light beam 112W) that has sufficiently larger numerical aperture ($\beta_{max}$) to refract out of the sample and to pass around a lower numerical blocking disk ($\beta_{min}$). The index-matching oil 330 and a reference block 320 are used to make sure that the light refraction occurs with the least amount of reflection from the edge surface 304 of the sample 300.

The refracted light power is measured across the thickness of the sample 300, index-matching oil 330 and reference block 320 by moving the sample setup (i.e., the sample, the index-matching oil and the reference block) across the focus 260 of the first focused light beam 112F1 at a constant speed. Then the optical power values for the light passing through the index-matching oil 330 and reference block 320 at each point of the sample ($P_{sample}$) are measured. With the values of the optical power measured for the oil ($P_{oil}$), the reference block ($P_{ref}$), and the sample ($P_{sample}$), the refractive index of the sample ($n_{sample}$) at each point is calculated for both TE and TM modes using the following formula:

$$n_{sample} = \left(\frac{n_{ref} - n_{oil}}{P_{ref} - P_{oil}}\right) P_{sample} + n_{ref} - \left(\frac{n_{ref} - n_{oil}}{P_{ref} - P_{oil}}\right) P_{ref} \quad \text{(Eq. 2)}$$

where $n_{ref}$ and $n_{oil}$ are refractive indices for the reference block and for the oil, respectively.

By using the known SOC for the sample material under test and with the knowledge of the measured index profiles for the TM and TE polarized light, the birefringence and stress profiles across the sample are calculated using the above-mentioned relationship $S(x)=B(x)/SOC$.

The scanning of the sample 300 along its thickness (x-direction; see FIGS. 3A and 3B) can be performed in either continuous mode or in step by step mode. Details of the data collection process for each of these measurement modes is discussed below.

Example Signal Control and Processing System Configuration and Method

Figure 5:
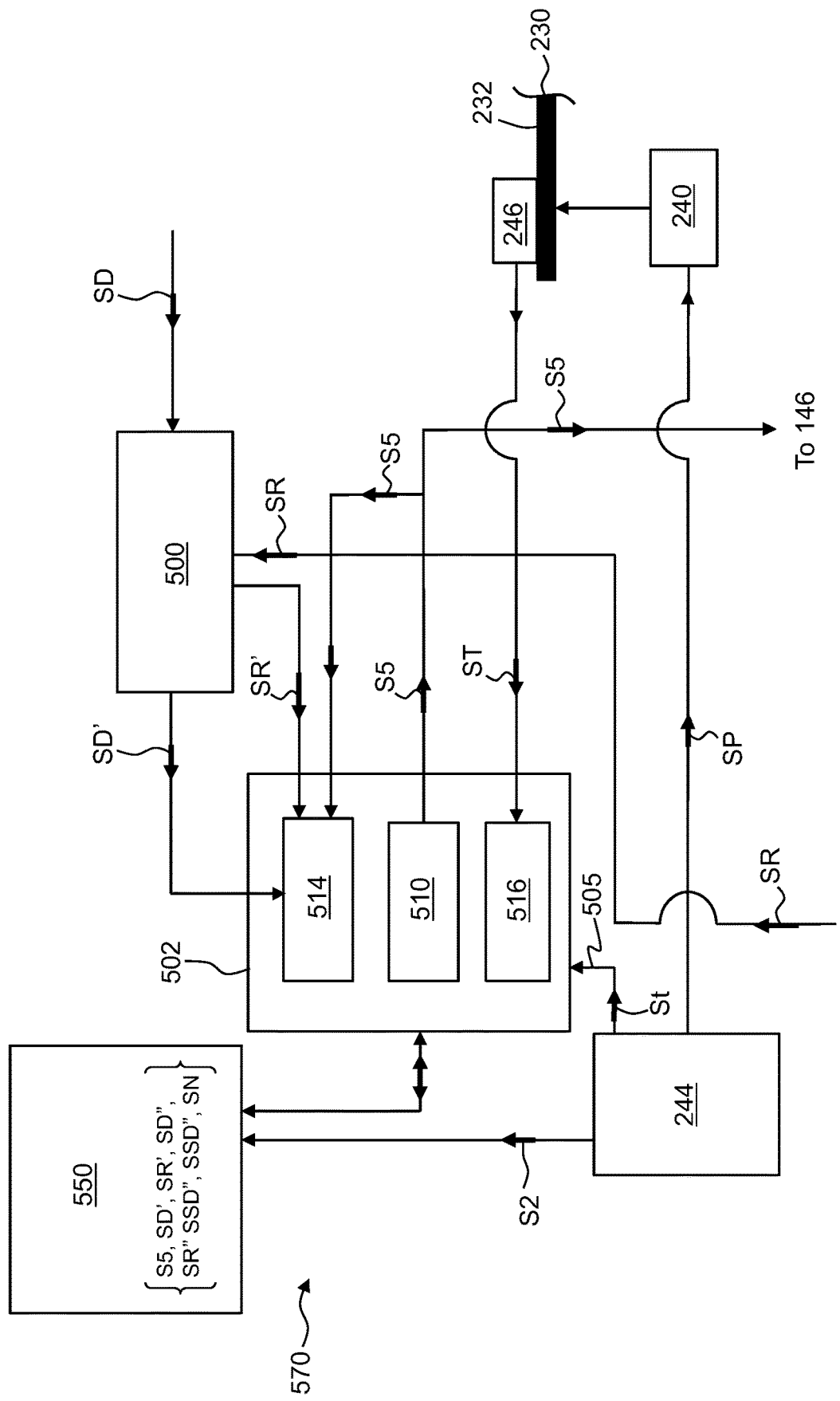
FIG. 5 is a schematic close-up diagram of an example configuration of the signal control and processing system of the RNF system, wherein the signal control and processing system includes an I/O controller that facilitates fast data processing of a large number of sample measurements and can comprise a cDAQ chassis or a cRIO chassis, depending on the measurement mode.

FIG. 5 is a schematic diagram of an example configuration of the signal control and processing system 570 of system 100. The signal control and processing system 570 shows an example I/O controller 502, which as noted above can comprise a chassis, such as a cDAQ chassis or a cRIO chassis, depending on the measurement mode (i.e., step or continuous, as discussed below). In an example, the stage controller 244 can be considered part of the signal control and processing system 570.

The I/O controller 502 also comprises the analog input card 514, such as the NI 9222 or the NI 9223 from National Instruments. The master-trigger controller 510 also comprises a digital I/O output card, such as the NI-9401 from National Instruments (e.g., with 8 DIO, 5 V/TTL, bi-directional, 100 ns). As noted above, the stage controller 244 is electrically connected to the positioning stage 240. The stage controller 244 is also electrically connected to the I/O controller 502 via an input line 505, which in an example can be a PFI (programmable function input) line or a DIO (digital input/output) line. The temperature input module 516 is electrically connected to the temperature sensor 246, which is in thermal communication with the movable support platform 230 for the reasons discussed above.

Figure 6:
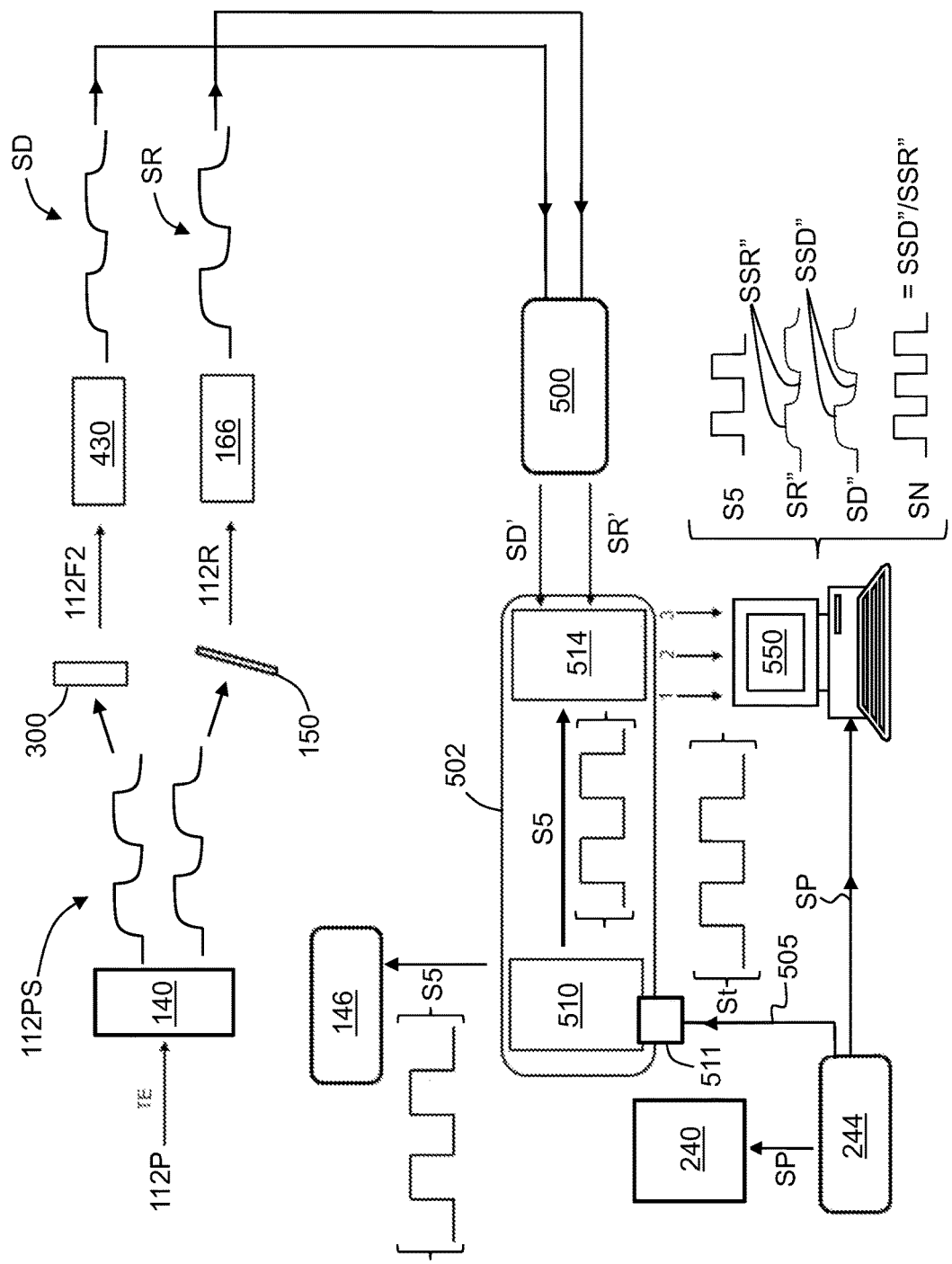
FIG. 6 is a schematic diagram of an example data collection method common to both the continuous mode and the step mode embodiments.

FIG. 6 is a schematic diagram of an example data collection method common to both continuous and step modes. By way of example, the polarization state of the polarized light beam 112P incident upon the FLC polarization switch 140 is set to TE (with respect to the measurement plane of the sample). The FLC polarization switch 140 is used to switch the state of polarization of the polarized light beam 112P between the TE and TM modes at a high frequency (e.g., between 1 kHz and 5 kHz) to define the polarization-switched light beam 112PS. The phase and frequency of the FLC polarization switch 140 are controlled through a digital control signal S5, which in an example is a TTL signal generated by the NI digital output card 510. The frequency and the phase of the TTL signal S5 are controlled through software settings (e.g., in the aforementioned LabVIEW® software). Both detector and reference signals SD an SR are collected using the reference and signal photodetectors 166 and 430, as described above. These signals pass through the gain adjuster 500, which amplifies the signals by a set gain. The gain-adjusted detector and reference signals SR' and SD' are then sent to the analog input card 514.

In addition, the TTL signal S5 is provided to the analog input card 514 to serve as a reference (phase) signal. The objective of the reference TTL phase signal S5 is to determine the phase of the TE and TM modes of the polarization-switched light beam 112PS, i.e., the start and end of TE and TM modes to define gain-adjusted synchronized detector and reference signals SD" and SR", where the synchronization is for the TE and TM components of these signals for the given measurement position. Steady-state portions SSD" and SSR" of the gain-adjusted and synchronized detector and reference signals SD" and SR" (as identified using the TTL signal S5, as explained below) are then used to define the measurement signal SN.

The position of the movable support platform 230 at each point is monitored through a software command or through a trigger (counter) signal St sent by the stage controller 244 to the I/O controller 502 via the input line 505 (details of how this trigger signal St is used to implement a trigger mode or non-trigger mode are discussed below). The input trigger signal St can be fed into a PFI input 511 of the I/O controller 502 or into one of the inputs of the NI digital output card 510.

The trigger signal St is used to synchronize the TTL signal S5, the gain-adjusted detector and reference signals SD' and SR', and the position of the movable support platform 230 (as embodied in the signal position SP) for both continuous and step modes. The PFI input 511 is a built-in trigger input in either a cDAQ or cRIO chassis and can be used to synchronize analog and/or digital input/output with the external trigger signal St.

Figure 7:
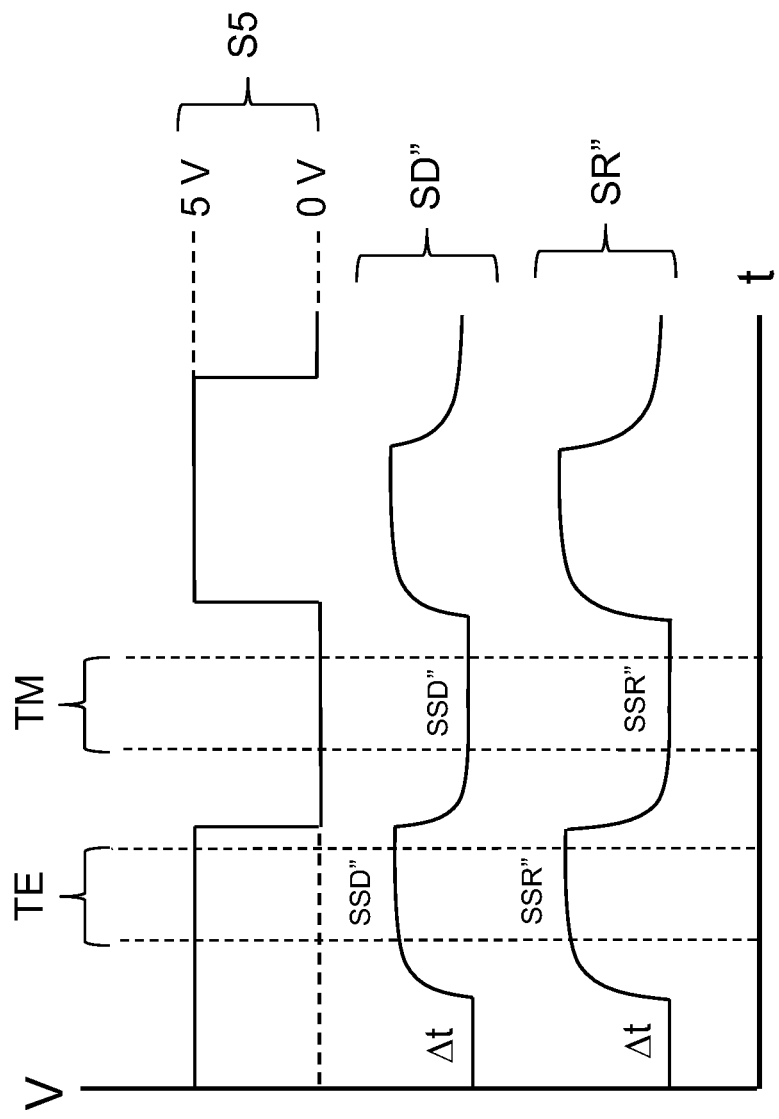
FIG. 7 is a generalized plot of voltage V versus time t showing example synchronized and gain-adjusted reference and detector signals SR" and SD", along with the TTL digital control signal S5 as collected by the analog I/O card of the I/O controller, illustrating how the TTL signal S5 is used to identify steady-state portions SSR" and SSD" of the synchronized and gain-adjusted reference and detector signals used to calculate a measurement signal SN=SSD"/SSR".

FIG. 7 is a generalized plot of voltage V versus time t showing example gain-adjusted and synchronized reference photodetector signals SR" and SD", along with the TTL signal S5 used to synchronize the gain-adjusted reference and detector signals SR" and SD". These signals are collected using the three analog inputs of the analog input card 514. The synchronization is performed by the main computer-controller 550. Both the gain-adjusted synchronized reference and detector signals SR" and SD" are delayed in relation to the TTL signal by a short time delay Δt. This time delay or phase lag originates in the delay in the response of the FLC polarization switch 140 and is constant or a given FLC switching frequency.

To eliminate adverse effects of the inherent response time of the FLC, the gain-adjusted and (TE, TM) synchronized detector and reference signals SD" and SR" are processed when these signals reach their steady states, respectively denoted by SSD" and SSR". This eliminates signal-processing errors due to the attenuation of the polarized light beam 112P when the system 100 is switching between TE and TM polarization states. Following this procedure, the intensity ratio between TE and TM states of the polarization-switched light beam 112PS (as embodied in the corresponding portions of the measurement signal SN) can be maintained constant throughout the measurement. The measurement signal SN is calculated using SSD" and SSR", i.e., SN=SSD"/SSR". As a result, a change in the TE and TM optical power ratio in the initial detector signal SD occurs only due to stress-based characteristics of the of the sample.

Continuous Mode Measurement

One mode of operation of the system 100 is when the system moves the sample 300 at a constant speed. This mode is referred to herein as the continuous measurement mode, or just the "continuous mode."

The continuous mode starts by the stage controller 244 and the positioning stage 240 initiating movement of the movable support platform 230 until it reaches a constant speed, at which point the data collection begins. The data collection can be performed using one of two continuous-mode methods, namely a continuous FLC mode (with the NI-cDAQ-based data acquisition system) and trigger-driven FLC mode (with NI-cRIO-based data acquisition system).

a. Continuous FLC Mode

The continuous FLC mode is characterized by a number of steps carried out in system 100. In this mode, the signal control and processing system 570 initiates movement of the positioning stage 240 by activating the stage controller 244.

Once the positioning stage 240 and the support platform 230 reach an initial position and a desired constant speed, the TTL signal S5 is sent from the NI digital output card 510 to the FLC polarization-switch controller 146, which in turn drives the FLC polarization switch 140. The FLC polarization switch 140 then starts to switch the state of polarization of the polarized light beam 112P between TE and TM modes at a given frequency (e.g. 1 kHz). In this mode, the FLC continuously oscillates the state of polarization of the light between TE and TM mode until the measurements are completed.

Once the measurement starts at the initial measurement point, the X-Y position and the primary three analogue signals (TTL signal S5 and the gain-adjusted reference and detector signals SR' and SD') are continuously received by the analog input card 514 of the I/O controller 502, with the gain-adjusted measurement and reference signals coming from the gain adjuster 500 and the TTL signal S5 coming from the digital output card 510.

The X-Y position of the sample 300 is obtained through software commands accessible via the stage controller 244. With the position signal SP provided from the stage controller to the I/O controller 502. The time gap $\Delta t$ between the X-Y position detection and the analog signal detection is typically in the range of a few microseconds, so the positional error associate with this procedure is insignificant (e.g. a 10 μs time gap at motion speed of 0.02 mm/s results in a 0.2 nm error spatial inaccuracy). The data collection occurs continuously while the data is being processed (consumed) in parallel by the I/O controller 502 using parallel processing software algorithms known in the art. For example, the aforementioned LabVIEW® software can be used for parallel processing the data.

The analog input card 514 is used to collect the primary analog signals SD' and SR' at high speed, e.g., about 500K samples/second. In an example, the analog input card 514 and digital output card 510 are inserted into and supported by a NI cDAQ chassis (NI cDAQ-9178). As described above in connection with FIG. 7, the TTL signal S5 is used as a reference signal to differentiate between the light intensities (signal values) for TE and TM polarizations when forming the measurement signal SN.

The sampling and data acquisition accounts for the sample speed, FLC polarization switch frequency, and the desired spatial resolution/accuracy desired. As an example, if the positioning stage (and thus the sample 300) moves at a constant speed (e.g. 0.02 mm/s) and the FLC polarization switch 140 operates at 1 kHz. To cover both the TE and TM modes, then at least 1 ms worth data corresponding to 500 data points in the time domain (for the data acquisition speed 500K samples/second/channel) is captured. The sampling for this example case is large enough to measure both TE and TM polarized light intensities. During the measurement time, the sample moves 20 nm, which is insignificant compared to the spatial resolution of the optical system, which is about 500 nm for the blue 405 nm wavelength of the initial light beam 112 from the light source 110.

b. Trigger-Driven FLC Mode with NI-cRIO Data Acquisition System

In the trigger-driven FLC mode, the sample 300 is in constant motion at a select speed, referred to as the measurement speed. The trigger signal St from the stage controller 244 (see FIG. 5) is used to detect the sample position, to activate the FLC polarization switch 140, and to trigger the data acquisition process when the sample reaches the measurement speed.

In an example, the stage controller 244 generates a trigger signal St each time it moves the positioning stage 240 (and thus the sample 300) by a select (e.g., predetermined) distance $\Delta x$, such as every 200 nm. Once the positioning stage 240 reaches its initial measurement position, the trigger signal St is enabled through a software command (e.g., a one-time trigger enable). Each time the positioning stage 240 moves, the predetermined (pre-programmed) distance $\Delta x$, the stage controller 244 automatically sends the trigger signal St to the I/O controller 502 and in particular to the PFI input 511 of the NI-cRIO chassis (i.e., I/O controller 502) or one of the inputs of the digital output card 510.

Once the cRIO chassis receives the trigger signal St, it causes the digital output card 510 to generate the TTL signal S5 and send it to the FLC polarization-switch controller 146. The data acquisition of the three primary analog inputs (namely, signals SD', SR' and S5) to the analog input card 514 are configured to be activated by the trigger signal St. Therefore, as soon as the analog input card 514 receives the trigger signal St, the data acquisition for a single measurement point of the sample 300 takes place. In this triggerdriven FLC mode, each trigger signal St corresponds to a new data (measurement) point. In the absence of any additional communication between the I/O controller 502 and the stage controller 244, in this mode much faster measurement can be achieved with high precision which in fact provides even more accurate, faster data collection than continues FLC mode that described previously. In addition, in this mode, in the absence of direct communication with motion stage controller (during the data acquisition) a much more robust software architecture can be implemented.

The ability to process a large number of measurement data points in a relatively short amount of time is enabled by the systems and methods disclosed herein in part by the combination of the parallel processing configuration of the I/O controller 502 that utilizes the external triggering signal St to synchronize the measurements with the sample positioning. The compact Ni-cRIO chassis used in the example of the I/O controller 502 is a combination of a real-time controller, reconfigurable input/out modules, FPGA modules and an Ethernet chassis. This platform enables high speed and deterministic data acquisition, leading to precise and well-controlled data collection of relatively large amounts of data in a short period of time.

Step Mode

In the step mode, the system 100 can be designed with or without a trigger signal St from the stage controller 244. In either case, the stage controller 244 is programmed to move the positioning stage 240 in the step mode, with each step having a select or predetermined distance $\Delta x$, e.g. 200 nm. Once the positioning stage 240 moves a single step distance, it comes to a complete stop until the stage controller 244 directs it to move again. The position and status of the positioning stage 240 can then be monitored using the trigger signal St or through software commands.

Unlike the continuous mode, in the step mode, data collection of the detector signal SD, the reference signal SR and the TTL signal S5 occurs once the positioning stage 240 (and thus the sample 300) comes to a complete stop. The FLC polarization switch 140 can be operated in either continuous mode or it can be triggered by using the trigger signal St from the stage controller 244. In the case of trigger mode, the length of the TTL signal S5 (in the time domain) should cover, at minimum, the time relative to the acquisition of the detector and reference signals SD and SR for the TE and TM states (see, e.g., FIGS. 5 and 6).

In an example, for a TTL signal S5 with a frequency of 1 kHz, the TTL signal should be at least 1 millisecond (ms) long. On the other hand, for the case where the FLC polarization switch 140 operates in continuous mode, the data collection can be activated through software commands. In either case, the TE and TM portions of the gain-adjusted detector signals SD' can be separated by utilizing the phase information of the TTL signal. In this mode, the measurement time is dictated by the motion time per single movement step. For example, the measurement time can be 50 ms for a 200 nm step, which is significantly higher when compared to the data collection time that is in the order of 1 ms for a 1 kHz FLC frequency.

Conversion of the Optical Power Signal to Refractive Index

In system 100, the detector signal SD and the reference signal SR are processed by the gain adjuster 500 (e.g., a dual-channel power meter, such as the one from Newport Instruments identified as model 2936-R) so that the voltages of these signals are representative of their measured optical powers. In an example, the conversion of the output voltage of the detector and reference signals SD and SR into the gain-adjusted versions of these signals having voltages corresponding to the measured optical power is performed by using following relationship (EQ. 3):

$$P_{optical}(W) = \frac{V_{measured}(V) * \text{Conversion\_Factor}(A/V)}{\text{Detector\_Responsivity}\left(\frac{A}{W}\right)} \quad [\text{EQ. 3}]$$

where $V_{measured}$ is the measured optical power and Detector_Responstivity is the calibrated detector responsivity provided by the detector manufacturer. The Detector_Responstivity is a function of the wavelength of the light that is being used and these calibration values are provided by the detector manufacturer. The Conversion_Factor is for the specific power detector that is used in the system 100 and depends on the input resistance of the data acquisition system (in this case, >1 GΩ) and the range (gain) in the power meter settings.

Figure 8A:
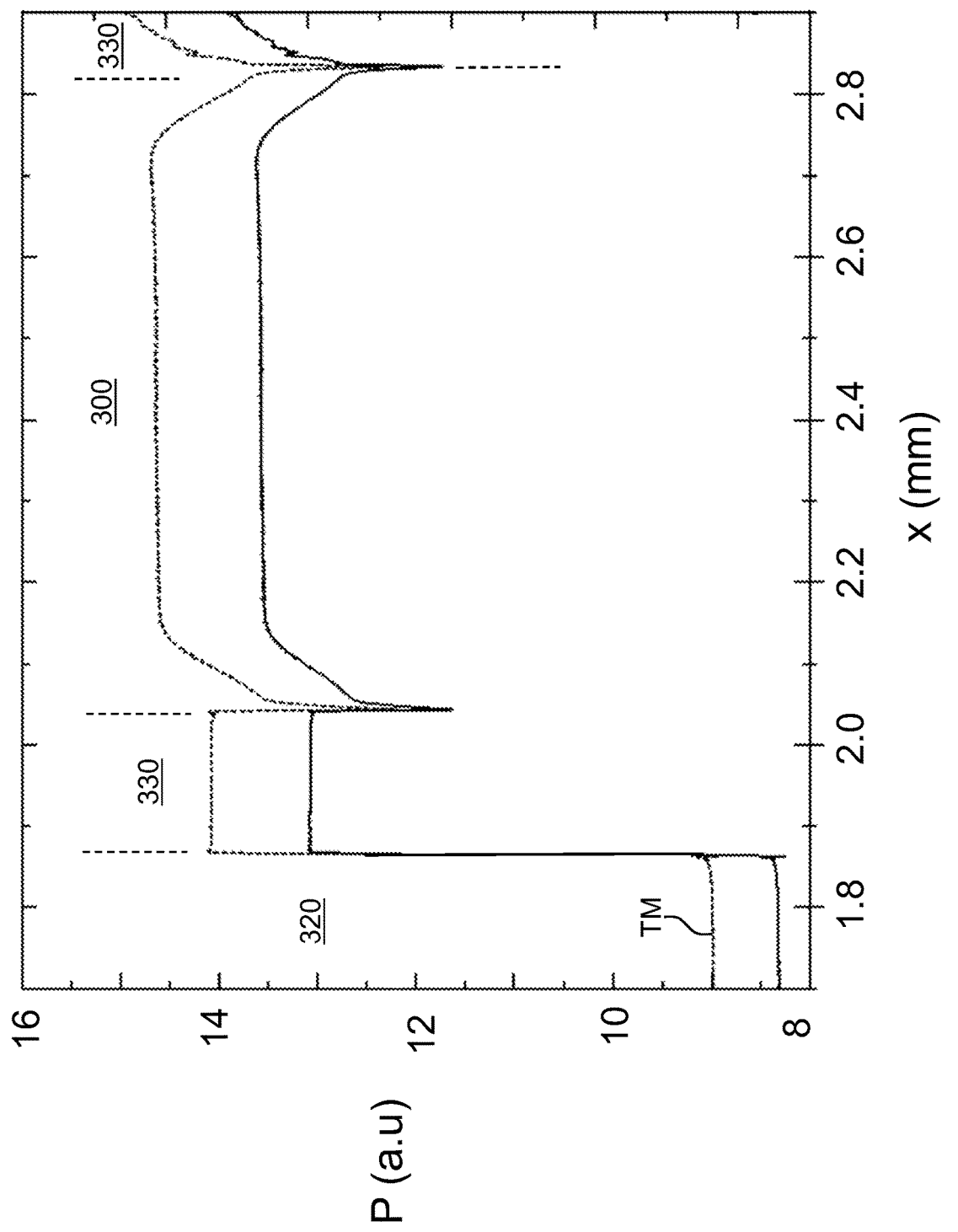
FIG. 8A is a plot of the optical power $P_{optical}$ (arbitrary units) (left-hand vertical axis) and the refractive index n (right-hand vertical axis) versus position x (mm) for an example measurement scan of an example sample.
Figure 8B:
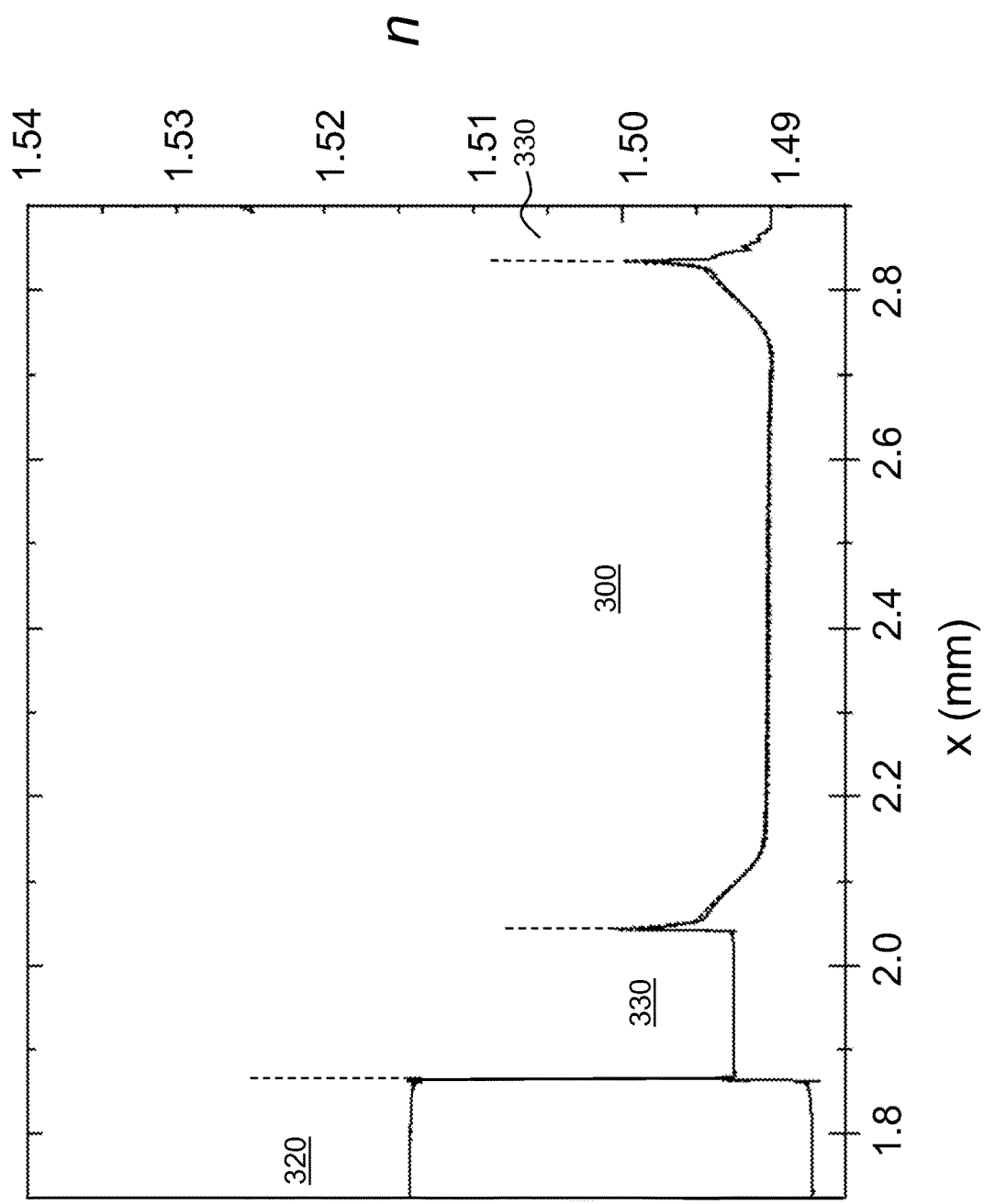
FIG. 8B is a plot of refractive index n versus position x (mm) for the same example glass sample as in FIG. 8A.

FIG. 8A is a plot of the optical power $P_{optical}$ (arbitrary units) versus position x (mm) for an example measurement scan of an example sample 300. FIG. 8B is a plot of the refractive index n versus the position x (mm) for the same example sample 300 of FIG. 8A The ambient temperature near the sample 300 is acquired at the beginning of each measurement cycle using the temperature sensor 246 and the temperature input module 516. The measured temperature as embodied in the temperature signal ST is used to correct for the refractive index of the index-matching oil 330 and the reference block 320 using a previously known relationship for the dn/dT for these materials.

In an example, the temperature sensor 246 comprises an Omega contact thermocouple, while the aforementioned A NI-9210 C series temperature input module is inserted into the cDAQ chassis (I/O controller 502) and used to acquire the temperature data from the thermocouple. The temperature variation during a single measurement is typically less than 0.1° C., which is too small to have a substantial impact in the measurement. This is because the change in refractive index as a function of temperature (i.e., dn/dT) for the index-matching oil 330 and for the reference block 320 is about 0.0004° C. and about 0.000002° C., respectively. The 0.1 degree variation can change the refractive index of oil only by 0.002%. Therefore, for the 1-D scan, in an example the temperature measurement is performed only at the beginning of each scan.

By using the known (and stored) dn/dT properties of the index-matching oil 330 and the reference block 320 and by subsequently measuring the optical power of the detector and reference signals SD and SR, the refractive index profiles for the test sample 300 for TE and TM modes can be calculated using Eq. (2), above. By this procedure, the refractive index profiles for the TE polarized light ($n_{TE}$) and the TM polarized light ($n_{TM}$) are measured across the thickness of the sample under test (i.e., $n_{TE}(x)$ and $n_{TM}(x)$), where x is the direction into the sample 300. With the knowledge of the stress-optic coefficient (SOC) of the material under test and by using the measured birefringence $B(x)=n_{TM}(x)-n_{TE}(x)$, the stress profile S(x) across the sample can be finally calculated via $S(x)=B(x)/SOC$.

Post Processing

Aspects of the disclosure are directed to post-processing of the collected measurement data. A number of example post-processing steps are now discussed.

A. Slope Correction for Optical Power Curve

One goal of the post-processing steps is to correct any errors associated with absorption loss as light propagates through different materials, including the sample 300, the index-matching oil 330 and the reference block 320, as well as from imperfections in the other optical and opto-mechanical components of the system 100. As a result of such system imperfections, the slope of the optical power vs. position curve can change and introduce a minor error in estimating the TM and TE refractive indices $n_{TM}(x)$ and $n_{TE}(x)$, and subsequently the stress S(x).

The following example procedure can be used to reduce or correct the slope error in the measured optical power curve (profile).

Figure 8C:
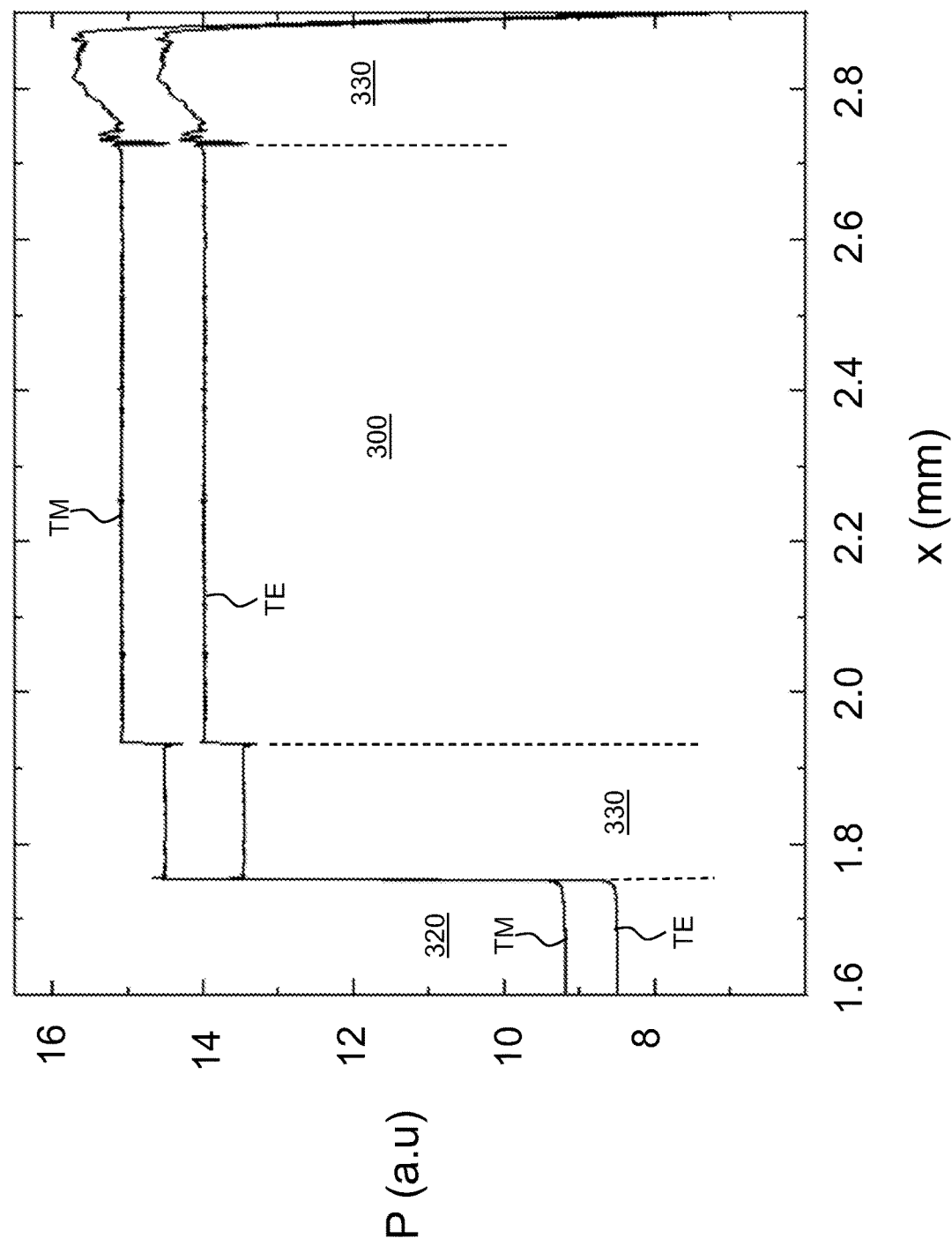
FIG. 8C is similar to FIG. 8A and shows the optical power profiles for a non-IOX reference sample.

1) measure the optical power profiles of a similar sample (reference sample) of the same thickness as the sample 300 to be measured but that has not undergone an IOX process (or other stress-inducing process), i.e., the sample has no stress-based characteristics. FIG. 8C is similar to FIG. 8A and shows the optical power profiles for a non-IOX reference sample. In the absence of an IOX-induced refractive index variation, the optical power curves of the non-IOX glass reference sample, the index-matching oil 330 and a reference block 320 should be flat, except at the interface between the sample 300 and reference block 320.

2) The slope for each region of the optical power curves is then determined, along with the location of the interface between the sample 300 and reference block 320.

3) Calculate the slope correction for each point of the optical power curve using following formula:

$$P_{corrected} = P_{measured} + \text{Bias}(X_{edge})$$

where $P_{corrected}$ and $P_{measured}$ are corrected and measured optical power, respectively. Bias ($x_{edge}$) is the system bias BIAS at distance $X_{edge}$ from the interface and it can be expressed by following polynomial equation $$BIAS(x=d) = \sum_{n=0}^{n=m} A_n X_{edge}^{n=m}$$

where n is a positive integer and $A_n$ is a coefficient (here, n is used as mathematical tracking subscript and not for the index of refraction). Similar slope correction can be applied for other regions including for the oil and reference cell area.

B. Extrapolation of the Stress Profile S(x)

The spatial resolution of the system 100 is limited by the optical configuration and the wavelength of the light used in the system. Therefore, system 100 has some limitations regarding measurement of stress near and/or at the surface of the sample 300. For example, with a blue laser, only values 500 nm below the edge surface 304 and with a red laser only approximately 1 μm below the surface edge can be properly measured.

Figure 9:
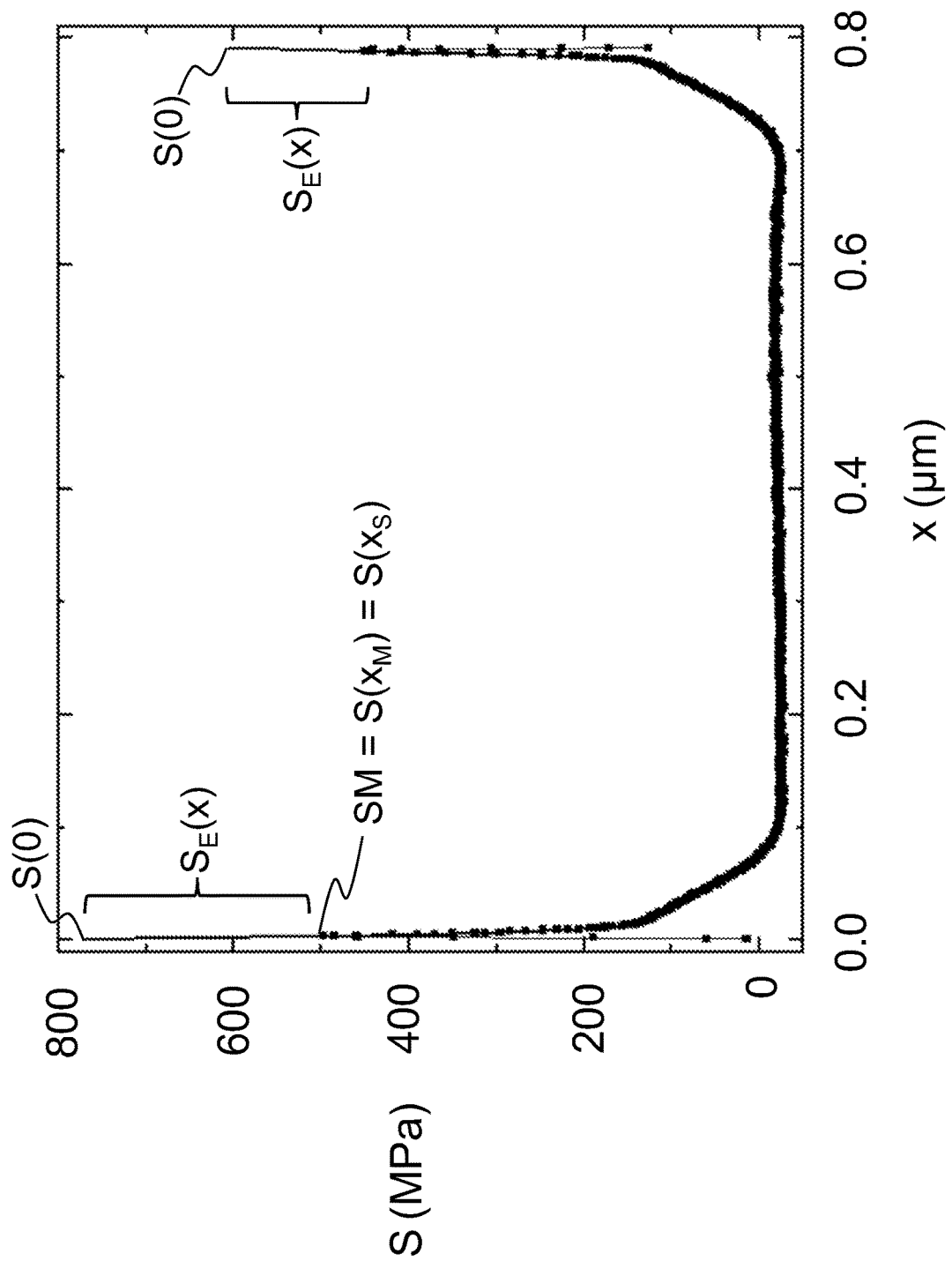
FIG. 9 is a plot of the (compressive) stress S(x) (MPa) as a function of the position x (mm) for the measured profile (connected circles) and the extrapolated profile $S_E(x)$ (solid line) for an example glass IOX sample.

FIG. 9 is a plot of the stress S(x) (MPa) as a function of the position x (mm) for the measured profile (connected dots) and the extrapolated profile $S_E(x)$ (solid line) for an example glass IOX sample. The measured profile shows the stress S(x) falling off at the sample surface at x=0 mm. To determine the stress values S(x) at the surface (i.e., S(0)) and just below the surface, the stress curve S(x) is extrapolated to the surface by using a known surface stress value S(0) measured by other means, e.g., other systems (instruments) or a different technology other than RNF-based systems and technologies.

In an example, the extrapolated profile $S_E(x)$ starts from a depth $x_S \geq x_M$ wherein $x_M$ defines $SM=S(x_M)$, where SM is a maximum value of the stress profile S(x) near the surface (x=0). In an example where $x_C$ represents the center of the sample 300, then starting depth $x_S$ can be anywhere from $x_M$ to $x_C$.

In another example, the near-surface portion of the stress profile S(x) has a knee shape that defines an associated knee stress $S_k$ at a knee depth $x_k$ from the sample surface (x=0), and in an example, the starting depth $x_S$ can be anywhere from $x=x_M$ to $x=x_k$.

The assumption here is that the strong dip in the stress profile S(x) in the near-surface portion (e.g., within $x_M$=500 nm for blue light) as shown in the plot of FIG. 9 is not truly representative of the actual stress profile due to the aforementioned limitations in the RNF measurement for near-surface regions of the sample.

Figure 10:
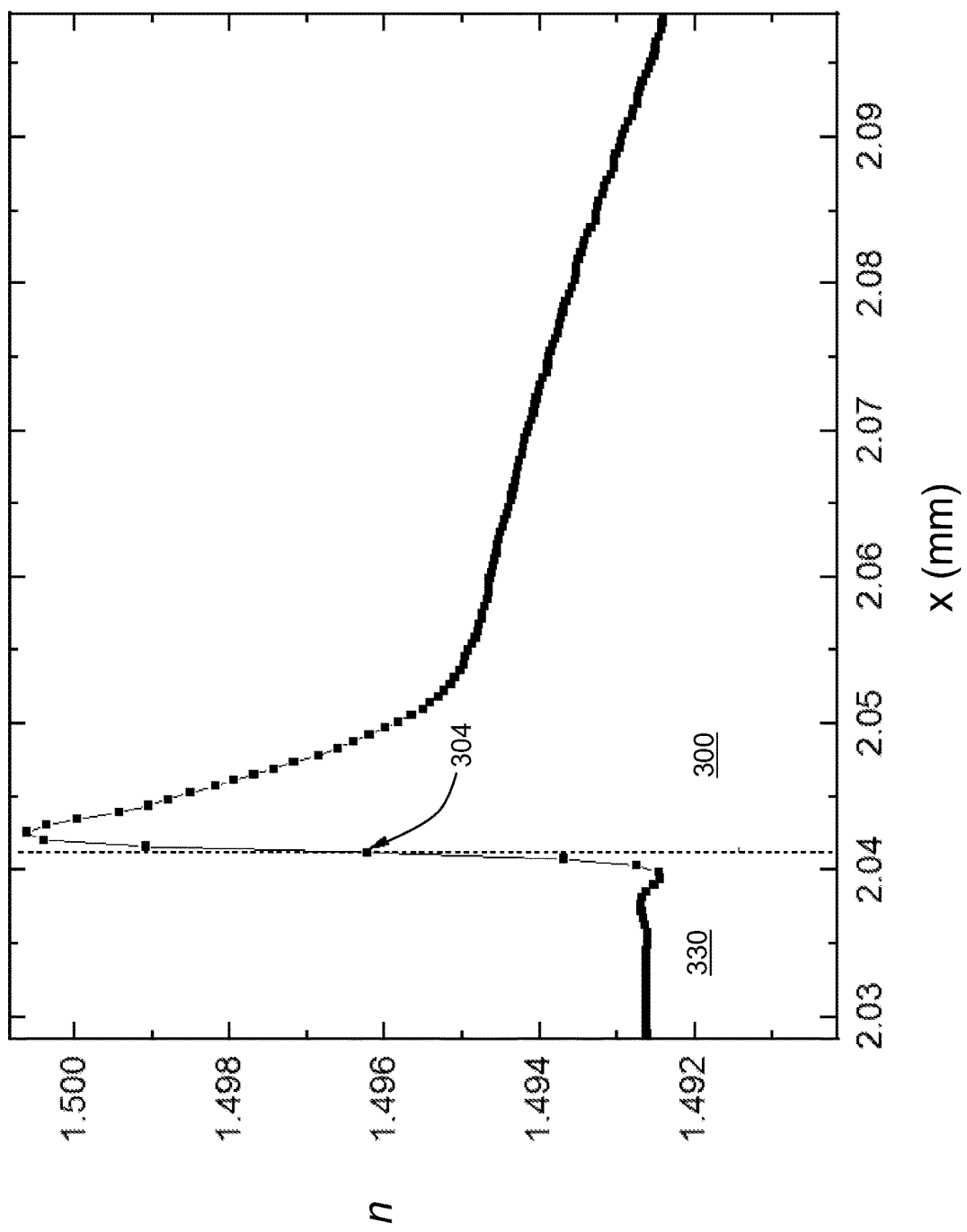
FIG. 10 is a plot of the refractive index n versus x position (mm) for the near-surface portion of a test sample.

FIG. 10 is a plot of the refractive index n versus x position (mm) for the near-surface portion of a test sample 300. As indicated in FIG. 10, the surface position of the test sample 300 can be selected at the center of the oil-glass interface by using the index profile measured by the system 100. With the surface position established from the data collected by the system 100 and the known stress values at the surface as measured independently (i.e., other than by system 100), the full stress profile S(x) can be obtained. More specifically, an extrapolation can be performed using linear, polynomial or other known extrapolation methods depending on expected stress profile S(x) of the test sample. The solid curve in FIG. 9 for example includes the linearly extrapolated portion $S_E(x)$ of the stress profile S(x) of the test sample 300 for the near-surface portion of the sample.

Force Balancing

It is known in the art that test sample, such as a glass test sample, in the absence of any external force is naturally force balanced. That is, in the absence of external forces, the total net stress across the sample must be zero, i.e., the integral of the total compressive stress is equal to the integral of the total tensile stress. However, due to optical imperfections in the system 100 and the intrinsic optical attenuation of measurement light by the sample across the light path, the system 100 can generate an unbalanced stress profile, which represents a measurement error.

To reduce or eliminate this measurement error, a post-processing method related to the force balance condition is introduced. The force balance post-processing can be performed on various portions of the stress profile S(x), such as for the left side of the profile, or for the full stress profile. Typically, the left-hand side of the stress profile (which is closer to the side of the reference block 320) is the side where the measurement is the most accurate.

In either case, the force balance can be done by moving the stress profile S(x) towards the compressive (positive) or tensile (negative) side until the total integrated stress is zero. In this step, as a result of moving stress profile up or down, the surface stress S(0) tends to change slightly. This can be corrected by using the extrapolation method described above. Some iteration may be required to make the surface stress S(0) and the force balance reach acceptable values. In an example, the integration of the stress curves is performed by using Simpson's rule.

During the force balance the stress curve moves up and down and as a result the surface stress of the extrapolated curves changes. Therefore, after completing the force balance, it is important to perform extrapolation again to re-establish the surface stress to its original value. However, depending on how much perturbation applied to the re-correction of the surface stress (extrapolation), the force balancing may also need to be reperformed. In general, both the force balance and extrapolation should be performed a sufficient number of times (N times) until both the surface stress and the force balance values are acceptable. Following the above steps produces the most accurate representation of the actual full stress profile and account for the best prediction of the total tensile and compressive stresses.

Figure 11A:
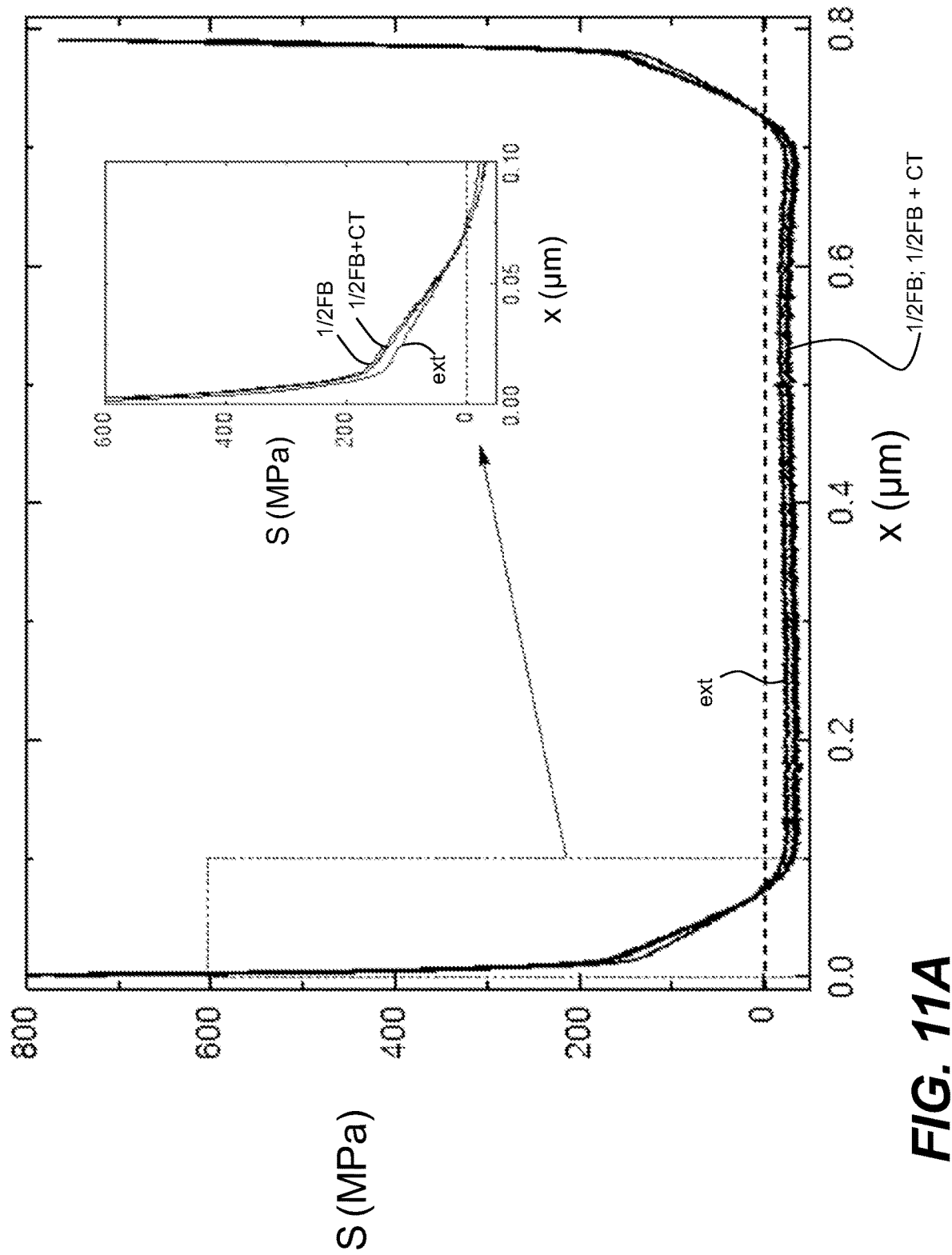
FIG. 11A is similar to FIG. 9 and shows the extrapolated stress profile S(x) along with a left-side force balance curve (i.e., half force balance or "½FB") and a half force balance curve with central tension (CT) correction, denoted "½FB+CT."

FIG. 11A is similar to FIG. 9 and includes an extrapolated stress profile S(x) along with a left-side (half) force balance curve (as indicated by "½FB"), which in the example performs the force balancing from the center of the sample to the surface. FIG. 11A also includes a half force balance curve with central tension (CT) correction, as indicated by "½FB+CT."

Figure 11B:
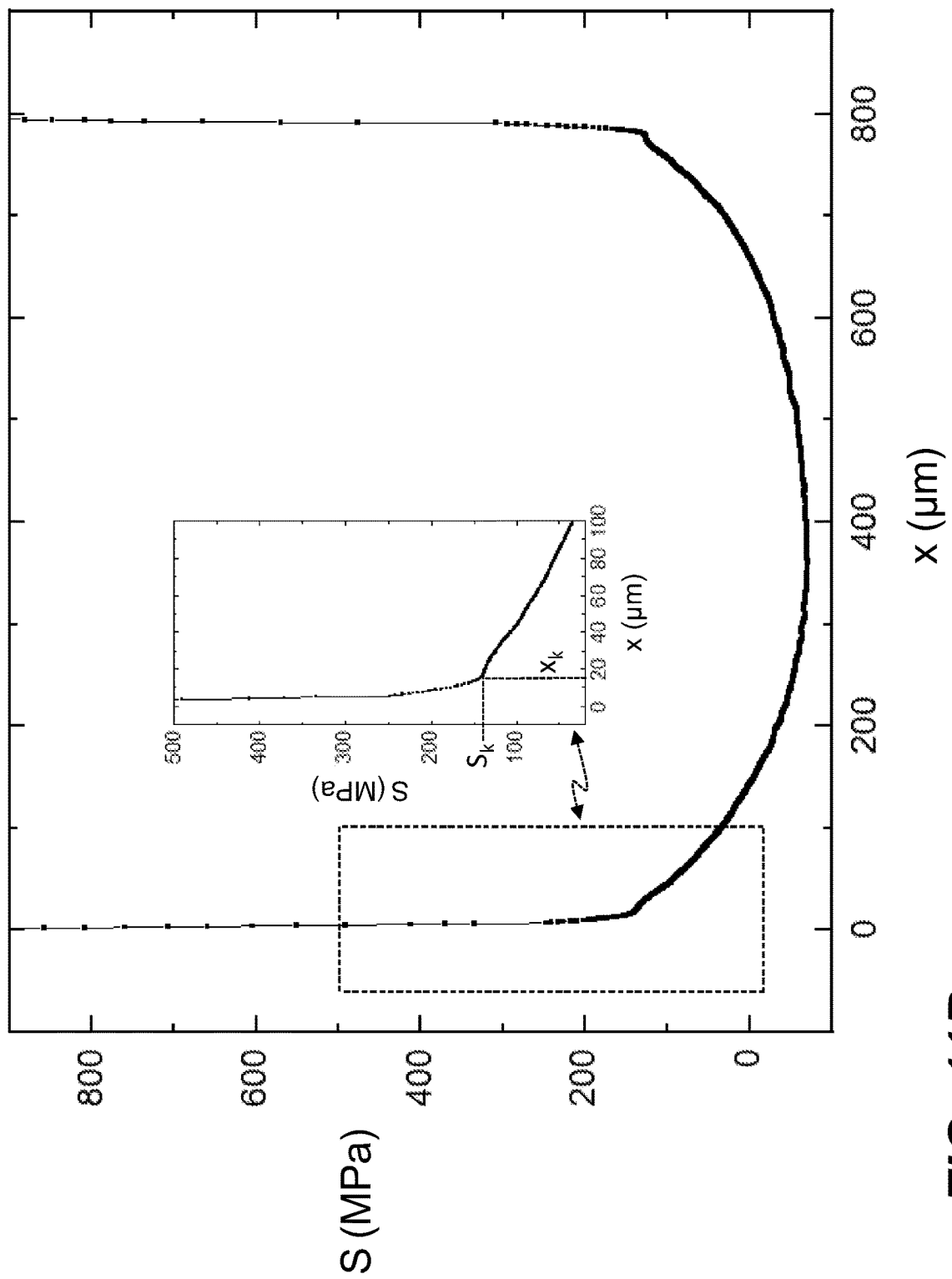
FIG. 11B is similar to FIG. 11A and plots the stress profile S(x) for an example IOX sample, with the close-up inset showing the near-surface portion of the stress profile that has a knee shape that defines an associated knee stress $S_k$ at a knee depth $x_k$ from the sample surface (x=0).
Figure 11C:
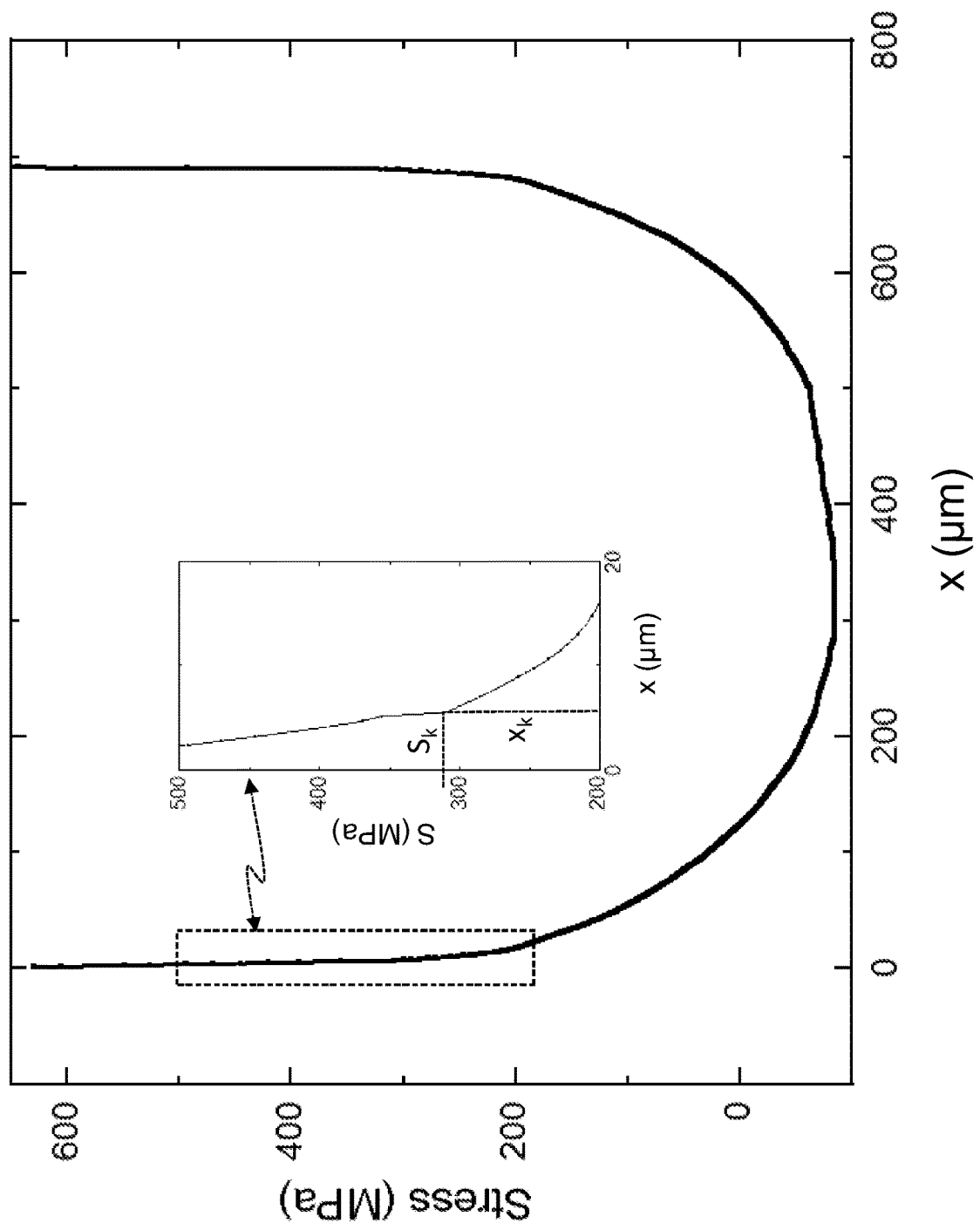
FIG. 11C is similar to FIG. 11B and shows the stress profile S(x) for another example sample, wherein the knee stress $S_k$ is about 310 MPa at a knee depth of about $x_k$=5 microns.

FIG. 11B is similar to FIG. 11A and plots the stress profile S(x) versus position x (mm) for an example IOX sample 300, with the close-up inset showing the near-surface portion of the stress profile that has a knee shape that defines an associated knee stress $S_k$ at a knee depth $x_k$ from the sample surface (x=0). The knee stress $S_k$ for the example IOX sample 300 of FIG. 11B is about $S_k$=145 MPa at a knee depth $x_k$ of about 15 microns from the sample surface. FIG. 11C is similar to FIG. 11B and shows the stress profile S(x) for another example IOX sample, wherein the knee stress $S_k$ is about 310 MPa at a knee depth of about $x_k$=5 microns.

Center Tension (CT) Correction

The center tension (CT) is the stress S at the center of the sample 300. If the center position of the sample is at $x=x_C$, then $CT=S(x_C)$. Imperfections in system 100 and in the polarization filtering can cause the center tension CT to deviate from its correct value.

The CT error can be estimated by measuring the center tension CT of a reference sample using the system 100. The reference sample is the same as the actual measured sample except that it has no substantial induced stress-based characteristics. For example, it is the same glass material as an IOX sample but has not undergone an IOX process. In the reference sample, the center tension CT is ideally zero. In fact, this knowledge can be used to assess the accuracy of the CT measurement in the system 100 since the measurement of CT for the reference sample should be zero. If the reference sample is measured by the system 100 to have an amount $CT_R$ of center tension CT (say, $CT_R$), then this measured amount $CT_R$ (which is actually supposed to be zero for a perfect system 100) is taken as a system offset and is used to correct the measured center tension of the IOX sample 300.

The correction of the center tension CT can be performed by multiplying the force-balanced stress profile S(x) by the ratio between the correct center tension CT measured by means other than system 100 (e.g., using a scattering polarimeter) and the measured CT of force-balanced stress profile measured by the system 100. In an example, multiple external measurements of the center tension CT are made and then averaged (e.g., 16 measurements) to independently establish the center tension CT value with reasonable accuracy and precision. FIG. 11A also shows the stress profile S(x) before and after CT correction performed as described above.

Two-Dimensional Stress Scan Capability

Figure 12A:
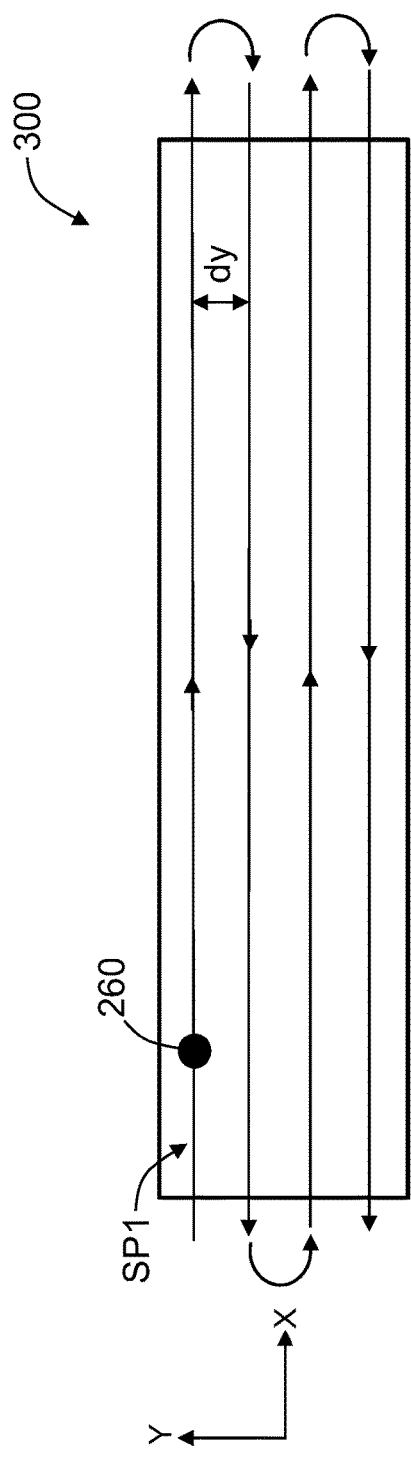
FIGS. 12A and 12B demonstrate two different scanning modes that utilize different scanning paths that can be utilized to establish a stress-based characteristic of a sample in two dimension (e.g., x and y, as shown).
Figure 12B:
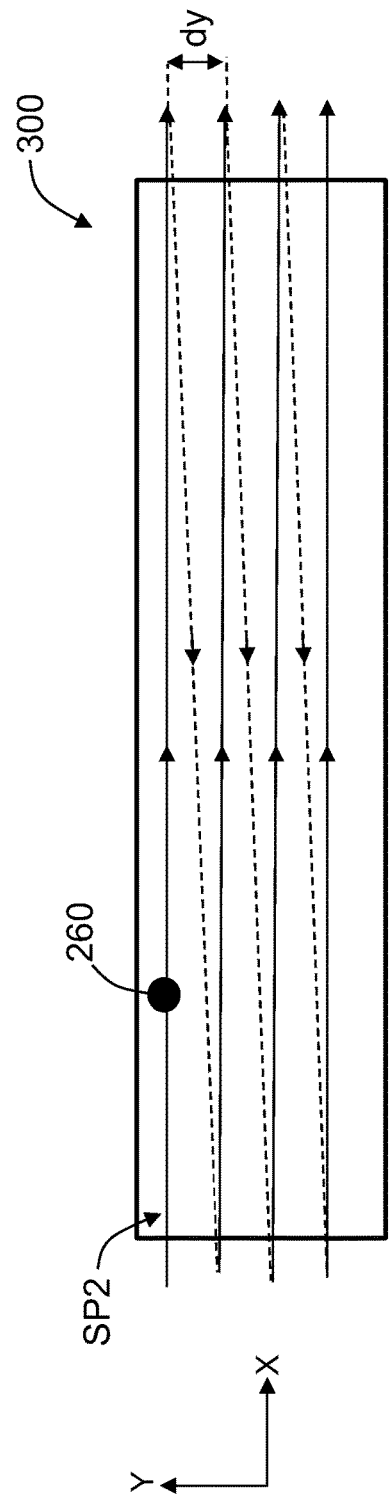

FIGS. 12A and 12B demonstrate two different scanning modes that utilize different scanning paths SP1 and SP2, respectively, that can be utilized to establish a stress-based characteristic of the sample 300 in two dimensions (e.g., x and y, as shown). The scanning paths SP1 and SP2 can be thought of as the movement of the focus 260 relative to the sample 300.

The scan path SP1 of FIG. 12A comprises a dual direction scan where the movement of the sample 300 over the entry point of the optical beam is done both in the x and y directions. The motion in the x-direction is done at a fixed position y until the end of the desired scan length in the x-direction. This is followed by a shift in the y direction by a step-size dy and the movement is resumed but now in the reverse x-direction going from the maximum excursion x back to the origin. This is followed by the same procedure multiple times as necessary to raster scan the area of interest of the sample 300. A main advantage of using the scan path SP1 is that the overall distance travelled is minimized and therefore it can lead to a reduction in measurement time.

The scan path SP2 of FIG. 12B scans in a single direction (e.g., the +x-direction, as shown) with retrace movement (dashed line) in the opposite direction but with an offset dy. During the retrace movement, no data is acquired. The movement to the new y-position can be done during the retrace as illustrated at the end or beginning of the retrace. This leads to the additional time of measurement as the retrace process does not acquire data. However, implementation and acquisition is much simpler with the integration of the positioning stage 240 of the system 100.

Continuous Mode and Step Mode Sampling

Figure 13A:
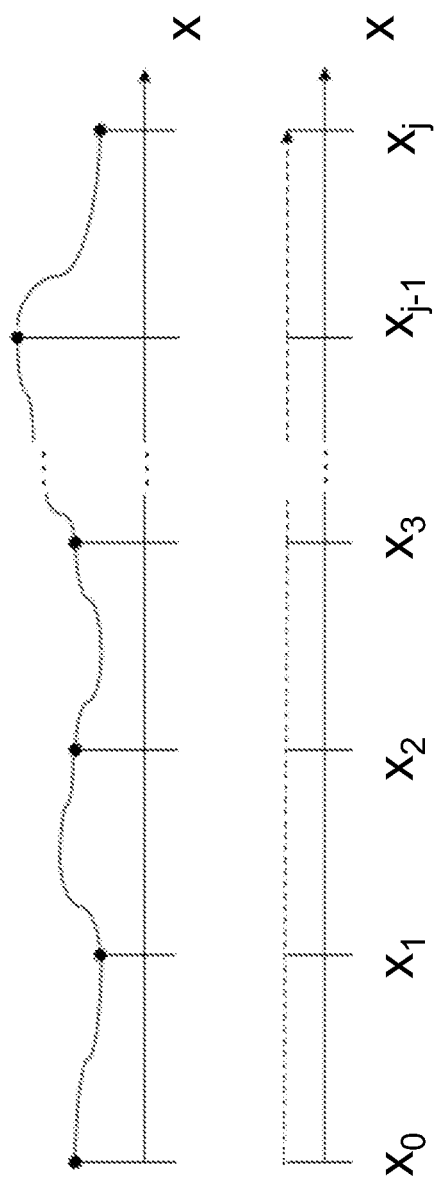
FIGS. 13A and 13B are schematic diagrams that illustrate the aforementioned continuous mode (FIG. 13A) and step mode (FIG. 13B) for data collection using the RNF system disclosed herein.
Figure 13B:
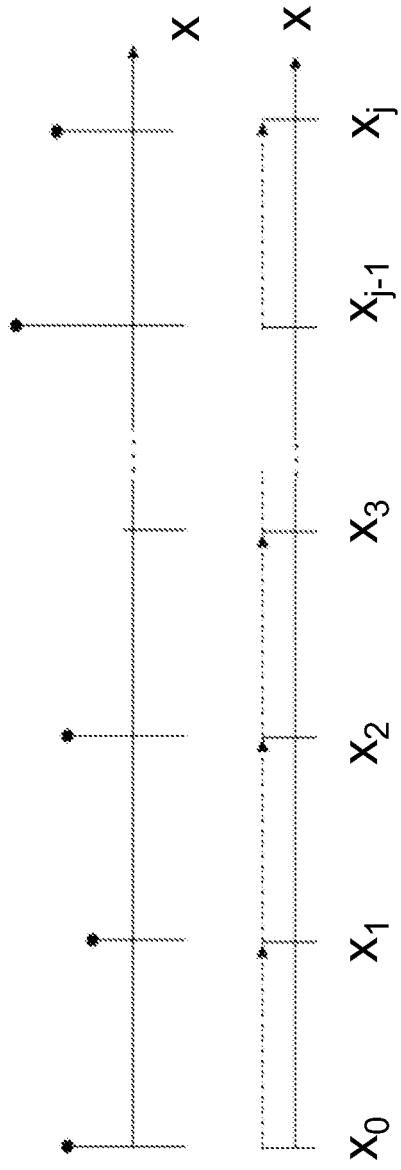

FIGS. 13A and 13B are schematic diagrams that illustrate the aforementioned continuous mode (FIG. 13A) and step mode (FIG. 13B) for the data collection methods using the system 100. With reference to FIG. 13A, at least one of the Cartesian directions x and y are measured continuously across not only the position $x_j$ but during the whole movement process before and after the desired position. The letter j is an index that represents the $j^{th}$ position. The x-coordinate is shown by way of example.

In this case, the polarization measurements are done also continuously using the continuous FLC mode or trigger-driven FLC mode. The final result is assigned a particular position $x_j$ based on the average of the measurements obtained during the movement around the desired position $x_j$. In the continuous acquisition mode, the sample 300 needs to reach the first measurement point at a constant measurement speed. Therefore, sample movement is initiated prior to the first point to allow the sample to ramp up to the measurement speed.

With reference to FIG. 13B, in the step (or discrete) mode, the sample 300 is stopped at a select position $x_j$. In this case, each polarization measurement is made when the system is stopped at the particular location (i.e., the $j^{th}$ location). Once the measurement for the discrete points is completed, the sample 300 is moved to the adjacent position by a select movement increment and the next measurement made. This process is repeated until the end of the desired length or area is measured.

It will be apparent to those skilled in the art that various modifications to the preferred embodiments of the disclosure as described herein can be made without departing from the spirit or scope of the disclosure as defined in the appended claims. Thus, the disclosure covers the modifications and variations, provided they come within the scope of the appended claims and the equivalents thereto.

What is claimed is:

1. A refracted near-field (RNF) measurement system used to measure at least one stress-based characteristic of a sample, comprising:
    a) a signal-generation section that generates a polarization-switched (PS) detector and reference signals SD and SR having a PS frequency representative of switching a measurement light beam between a transverse electric (TE) polarization and a transverse magnetic (TM) polarization;
    b) a signal-processing section in electrical communication with the signal-generation section and configured to receive and parallel process the PS detector and reference signals, the signal-processing section comprising:
        i) a gain adjuster configured to receive the PS detector and reference signals SD and SR and perform a gain adjustment to define gain-adjusted PS detector and reference signals SD' and SR';
        ii) a digital input/output (I/O) card configured to generate a digital control signal S5 that the defines the PS frequency;
        iii) an analog input card electrically connected to the gain adjuster and the digital I/O card and configured to receive the gain-adjusted PS detector and reference signals SD' and SR' and the digital control signal S5 and use the digital control signal to synchronize the PS gain-adjusted detector and reference signals to define PS gain-adjusted synchronized detector and reference signals SD" and SR" each having respective steady-state portions SSD" and SSR"; and
        iv) a computer/controller configured to:
            receive the PS gain-adjusted synchronized detector and reference signals SSD" and SSR" and using the steady-state portions SSD" and SSR" of these signals to define a measurement signal SN=SSD"/SSR"; and
            calculate the at least one stress-based characteristic using the measurement signal SN.

2. The RNF measurement system according to claim 1, wherein the gain adjuster is configured to provide the gain-adjusted PS detector and reference signals SD' and SR' with respective detector signal and reference signal voltages respectively representative of a detected optical signal power and a reference optical signal power.

3. The RNF measurement system according to claim 1, wherein the digital control signal has a timing, and wherein the signal generation section comprises a movable support platform that movably supports the sample, and a positioning stage that movably supports the movable support platform to define a sample position and a sample speed, and a stage controller that controls the positioning stage, and wherein the stage controller provides a trigger signal to the digital I/O card to set the timing of the digital control signal based on the sample position and the sample speed.

4. The RNF measurement system according to claim 3, wherein the positioning stage comprises a precision friction-driven piezoelectric-based motion stage.

5. The RNF measurement system according to claim 1, where the polarization switch comprises a ferroelectric liquid crystal (FLC) polarization rotator.

6. The RNF measurement system according to claim 1, wherein the reference signal is formed by detecting a reference optical signal emitted along a first optical axis that runs in a first direction, and wherein the reference optical signal does not undergo a reflection that changes the first direction of the first optical axis.

7. The RNF measurement system according to claim 1, wherein the analog I/O card and the digital I/O card are operably supported in either a cDAQ or cRIO chassis.

8. The RNF measurement system according to claim 1, wherein the signal-generation section comprises a polarization switch and wherein the PS detector signal travels through the sample while the sample moves at a constant speed and while operating the polarization switch continuously at the PS frequency.

9. The RNF measurement system according to claim 1, further comprising:
   a polarization switch in the signal-generation section;
   a positioning stage that supports the sample;
   a stage controller operably connected to the positioning stage and configured to control the position of the positioning stage to define different measurement positions; and
   wherein the PS detector signal travels through the sample while the sample moves at constant speed through the different measurement positions while being moved by the positioning stage controlled by the stage controller which generates a position signal representative of the different measurements positions, and wherein the stage controller generates a trigger signal to activate the polarization switch at the measurement positions.

10. The RNF measurement system according to claim 1, further comprising:
   a polarization switch in the signal-generation section;
   a positioning stage that supports the sample;
   a stage controller operably connected to the positioning stage and configured to control the position of the positioning stage to define discrete measurement positions; and
   wherein the PS detector optical signal travels through the sample while the sample is stepped to the discrete measurement positions as defined by the positioning stage controlled by the stage controller, wherein the stage controller generates a position signal representative of the discrete measurements positions, and wherein the stage controller generates a trigger signal to activate the polarization switch at the discrete measurement positions.

11. A method of measuring at least one stress-based characteristic of a sample having stress-induced characteristics using a refracted near-field (RNF) measurement system, comprising:
   generating polarization-switched (PS) detector and reference signals SD and SR having a PS frequency representative of switching a measurement light beam between a transverse electric (TE) polarization and a transverse magnetic (TM) polarization by detecting PS detector and reference optical signals having the PS frequency as defined by a polarization switch controlled by a digital control signal;
   performing a gain adjustment on the PS detector and reference signals SD and SR to define gain-adjusted detector and reference signals SD' and SR';
   using the digital control signal to synchronize the gain-adjusted PS detector and reference signals SD' and SR' to define gain-adjusted synchronized PS detector and reference signals SD" and SR" each having respective steady-state portions SSD" and SSR";
   using the steady-state portions SSD" and SSR" of these signals to define a measurement signal SN=SSD"/SSR"; and
   calculating the at least one stress-based characteristic using the measurement signal SN.

12. The method according to claim 11, wherein the at least one stress-based characteristic comprises at least one of: a birefringence, a stress profile, a surface stress, a knee stress and a center tension.

13. The method according to claim 11, wherein the PS detector optical signal travels through the sample while the sample moves at a constant speed and while operating the polarization switch continuously at the PS frequency.

14. The method according to claim 11, wherein the PS detector optical signal travels through the sample while the sample moves at constant speed through different measurement positions while being moved by a positioning stage controlled by a stage controller that generates a position signal representative of the different measurements positions, and wherein the stage controller generates trigger signal to activate the polarization switch at the measurement positions.

15. The method according to claim 11, wherein the PS detector optical signal travels through the sample while the sample is stepped to discrete measurement positions as defined a positioning stage controlled by a stage controller, wherein the stage controller generates a position signal representative of the discrete measurements positions, and wherein the stage controller generates a trigger signal to activate the polarization switch at the discrete measurement positions.

16. The method according to claim 11, wherein performing the gain adjustment comprises providing the gain-adjusted PS detector and reference signals SD' and SR' with respective detector signal and reference signal voltages respectively representative of a detected optical signal power for the detector optical signals and a reference optical signal power for the reference optical signals.

17. The method according to claim 11, comprising generating the reference optical signal along an unfolded first optical axis that runs only in a first direction, and detecting the reference optical signal along the first optical axis.

18. The method according to claim 11, further comprising:
   generating a sample optical power versus position curve for the sample using the measurement signal;
   creating a reference optical power versus position curve for a reference sample having no induced stress-based characteristics; and
   correcting the optical power versus position curve for the sample based on the reference optical power versus position curve.

19. The method according to claim 18, wherein said correcting comprises adjusting at least one slope in the sample optical power versus position curve.

20. The method according to claim 19, wherein the at least one slope is located at an interface between the sample and a reference block.

21. The method according to claim 11, where the polarization switch comprises a ferroelectric liquid crystal (FLC) polarization rotator.

22. The method according to claim 11, wherein the at least one stress-based characteristic comprises a stress profile S(x) that includes a near-surface portion to a depth $x_M$ into the sample wherein $SM=S(x_M)$, the method further comprising:
  measuring an amount of surface stress S(0) using a surface stress measurement system other than a RNF measurement system; and
  estimating the near-surface portion of the stress profile by forming an extrapolated portion $S_E(x)$ of the stress profile S(x) from a starting depth $x_S \geq x_M$ to x=0.

23. The method according to claim 22, wherein $x_C$ represents a middle of the sample, and wherein the starting depth $x_S \leq x_C$.

24. The method according to claim 22, wherein $x_k$ represents the position of a knee in the stress profile, and wherein the starting depth $x_S \leq x_k$.

25. The method according to claim 11, wherein the sample has a surface, a region of compressive stress, and a region of tensile stress, and wherein at least one stress-based characteristic comprises a stress profile S(x) with a total integrated stress, and further comprising:
  performing force balancing of the stress profile S(x) to define a force-balanced stress profile by adjusting a position the stress profile S(x) with respect to the compressive and tensile regions of the sample so that the total integrated stress is zero.

26. The method according to claim 25, wherein the stress profile S(x) includes a near-surface extrapolated portion $S_E(x)$ based on an independent measurement of a surface stress S(0) at the sample surface.

27. The method according to claim 25, wherein the performing of the force balancing is performed from a center of the sample to the surface of the sample.

28. The method according to claim 25, further comprising:
  using the RNF measurement system, performing a measurement of center tension in a reference sample that is substantially the same as the measured sample except known to have no substantial center tension to establish a RNF measurement system offset $CT_R$ for the measurement of center tension; and
  using the RNF measurement system offset $CT_R$ to adjust the force-balanced stress profile S(x).

29. The method according to claim 11, wherein the measurement light beam has a wavelength of 405 nm.

* * * * *

UNITED STATES PATENT AND TRADEMARK OFFICE
CERTIFICATE OF CORRECTION

PATENT NO. : 11,442,008 B2  
APPLICATION NO. : 16/944748  
DATED : September 13, 2022  
INVENTOR(S) : Norman Henry Fontaine et al.

Page 1 of 1

It is certified that error appears in the above-identified patent and that said Letters Patent is hereby corrected as shown below:

On the Title Page

Item (73), in Column 1, in "Assignee", Line 1, delete "Coming, NY" and insert -- Corning, NY --.

Signed and Sealed this  
Fourth Day of April, 2023

Katherine Kelly Vidal  
*Director of the United States Patent and Trademark Office*